US011591621B2

(12) United States Patent
Yamagata et al.

(10) Patent No.: US 11,591,621 B2
(45) Date of Patent: Feb. 28, 2023

(54) METHOD OF TREATING DISEASES ASSOCIATED WITH ELEVATED KRAS EXPRESSION USING CRISPR-GNDM SYSTEM

(71) Applicant: Modalis Therapeutics Corporation, Chuo-ku (JP)

(72) Inventors: Tetsuya Yamagata, Cambridge, MA (US); Yuanbo Qin, Cambridge, MA (US); Haruhiko Morita, Cambridge, MA (US); Talha Akbulut, Cambridge, MA (US); Iain Robert Thompson, Cambridge, MA (US)

(73) Assignee: Modalis Therapeutics Corporation, Chuo-ku (JP)

( * ) Notice: Subject to any disclaimer, the term of this patent is extended or adjusted under 35 U.S.C. 154(b) by 393 days.

(21) Appl. No.: 16/483,997

(22) PCT Filed: Feb. 7, 2018

(86) PCT No.: PCT/JP2018/004277
§ 371 (c)(1),
(2) Date: Aug. 6, 2019

(87) PCT Pub. No.: WO2018/147343
PCT Pub. Date: Aug. 16, 2018

(65) Prior Publication Data
US 2019/0376088 A1 Dec. 12, 2019

Related U.S. Application Data

(60) Provisional application No. 62/626,232, filed on Feb. 5, 2018, provisional application No. 62/455,845, filed on Feb. 7, 2017.

(51) Int. Cl.
| | |
|---|---|
| *C07H 21/02* | (2006.01) |
| *C07H 21/04* | (2006.01) |
| *C12N 15/90* | (2006.01) |
| *A61P 35/00* | (2006.01) |
| *A61K 31/7105* | (2006.01) |
| *C12N 15/113* | (2010.01) |
| *C12N 15/86* | (2006.01) |
| *C12N 15/11* | (2006.01) |
| *C12N 9/22* | (2006.01) |

(52) U.S. Cl.
CPC ........ *C12N 15/907* (2013.01); *A61K 31/7105* (2013.01); *A61P 35/00* (2018.01); *C12N 9/22* (2013.01); *C12N 15/111* (2013.01); *C12N 15/1135* (2013.01); *C12N 15/86* (2013.01); *C12N 2310/20* (2017.05); *C12N 2740/16043* (2013.01)

(58) Field of Classification Search
CPC .......................... C12N 15/113; C12N 2310/20
See application file for complete search history.

(56) References Cited

U.S. PATENT DOCUMENTS

| | | | |
|---|---|---|---|
| 2014/0179770 A1 | 6/2014 | Zhang et al. | |
| 2014/0242699 A1 | 8/2014 | Zhang | |
| 2015/0020223 A1 | 1/2015 | Zhang et al. | |
| 2016/0201089 A1 | 7/2016 | Gersbach et al. | |
| 2016/0340661 A1* | 11/2016 | Cong .................. | C12N 15/907 |
| 2017/0107536 A1 | 4/2017 | Zhang et al. | |

FOREIGN PATENT DOCUMENTS

| | | | | |
|---|---|---|---|---|
| WO | WO 2010/131080 A1 * | 11/2010 | ........... | C12N 15/113 |
| WO | WO 2014/093622 A2 | 6/2014 | | |
| WO | WO 2014/197748 A2 | 12/2014 | | |

OTHER PUBLICATIONS

Thurtle-Schmidt et al. (Biochemistry and Molecular Biology Education, 2018, vol. 46, issue 2, 195-205).*
Puchta et al. (Genome Biol 17, 51, 2016, 1-3).*
Prior, I. A. et al., "A Comprehensive Survey of Ras Mutations in Cancer", Cancer Research, vol. 72, 2012, pp. 2457-2467.
Cutsem, E. V. et al., "Cetuximab and Chemotherapy as Initial Treatment for Metastatic Colorectal Cancer", The New England Journal of Medicine, vol. 360, 2009, pp. 1408-1417.
Lièvre, A. et al., "KRAS Mutations as an Independent Prognostic Factor in Patients With Advanced Colorectal Cancer Treated With Cetuximab", Journal of Clinical Oncology, vol. 26, 2008, pp. 374-379.
Amado, R. G. et al., "Wild-Type KRAS is Required for Panitumumab Efficacy in Patients With Metastatic Colorectal Cancer", Journal of Clinical Oncology, vol. 26, 2008, pp. 1626-1634.
Cox, A. D. and Der, C. J., "Ras Family Signaling", Cancer Biology and Therapy, vol. 1, 2002, pp. 599-606.
International Search Report dated Apr. 3, 2018 In PCT/JP2018/004277 filed Feb. 7, 2018.
Les Henderson, et al., "KRAS gene amplification to define a distinct molecular subgroup of gastroesophageal adenocarcinoma.," Journal of Clinical Oncology, Retrieved from Internet [URL: https://ascopubs.org/doi/abs/10.1200/jco.2016.34.4_suppl.74] vol. 34, No. 4, Abstract No. 74, 2016, 5 Pages.
Luke A. Gilbert, et al., "Genome-Scale CRISPR-Mediated Control of Gene Repression and Activation," Cell, vol. 159, Oct. 23, 2014, pp. 647-661.

* cited by examiner

*Primary Examiner* — Amy H Bowman
(74) *Attorney, Agent, or Firm* — Oblon, McClelland, Maier & Neustadt, L.L.P.

(57) ABSTRACT

The present invention provides a method of treating a disease associated with elevated KRAS activity or expression in a subject, comprising suppressing KRAS expression in the subject by targeting an expression regulatory region of KRAS gene using a CRISPR-Guide Nucleotide Directed Modulation (GNDM). Also, provided is a CRISPR-GNDM system for suppressing KRAS expression comprising (a) a protein selected from the group consisting of dCas9 or dCpf1, a fusion protein of dCas9 or dCpf1 and Kruppel associated box (KRAB), and (b) a guide nucleotide targeting an expression regulatory region of KRAS gene.

8 Claims, 8 Drawing Sheets

Specification includes a Sequence Listing.

KRAS gene suppression by dCas9-KRAB fusion protein

Suppression of KRAS gene by dCas9-KRAB fusion protein and sgRNA 23-40

Figure 5
PANC1 cell proliferation assay
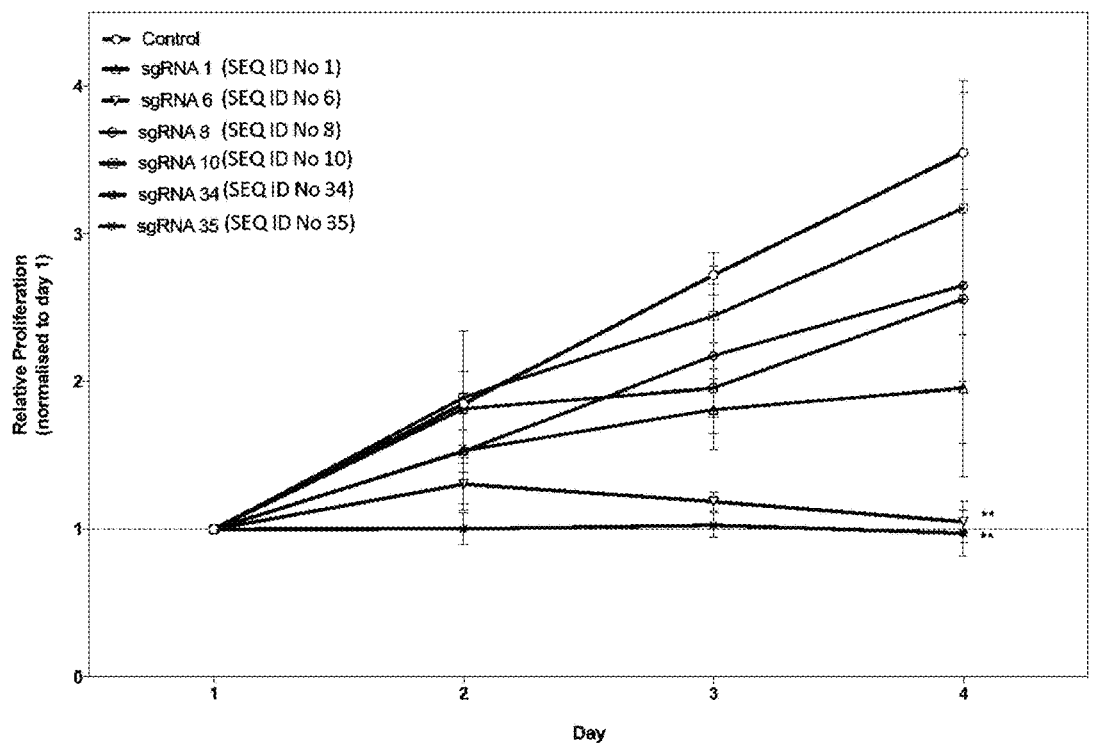
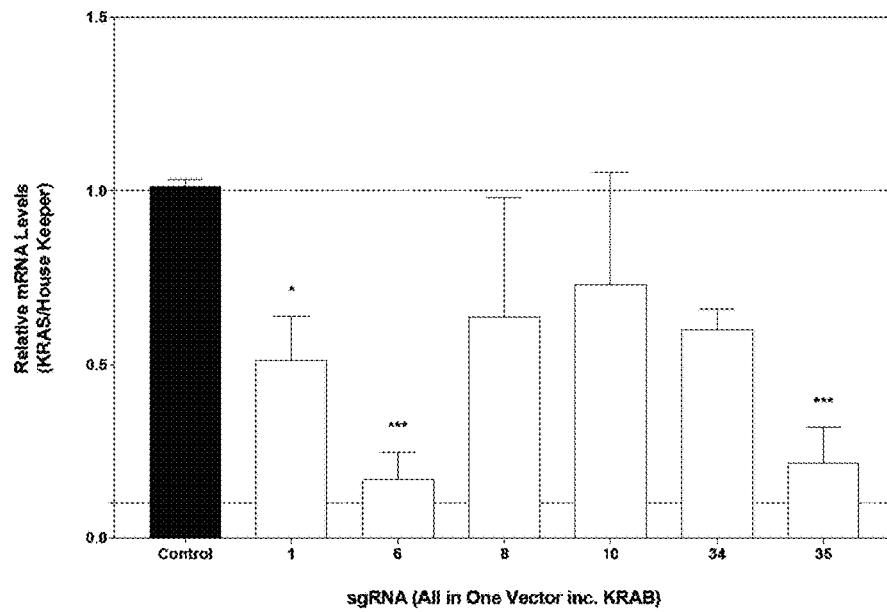

Figure 6
MiaPaca2 cell proliferation assay
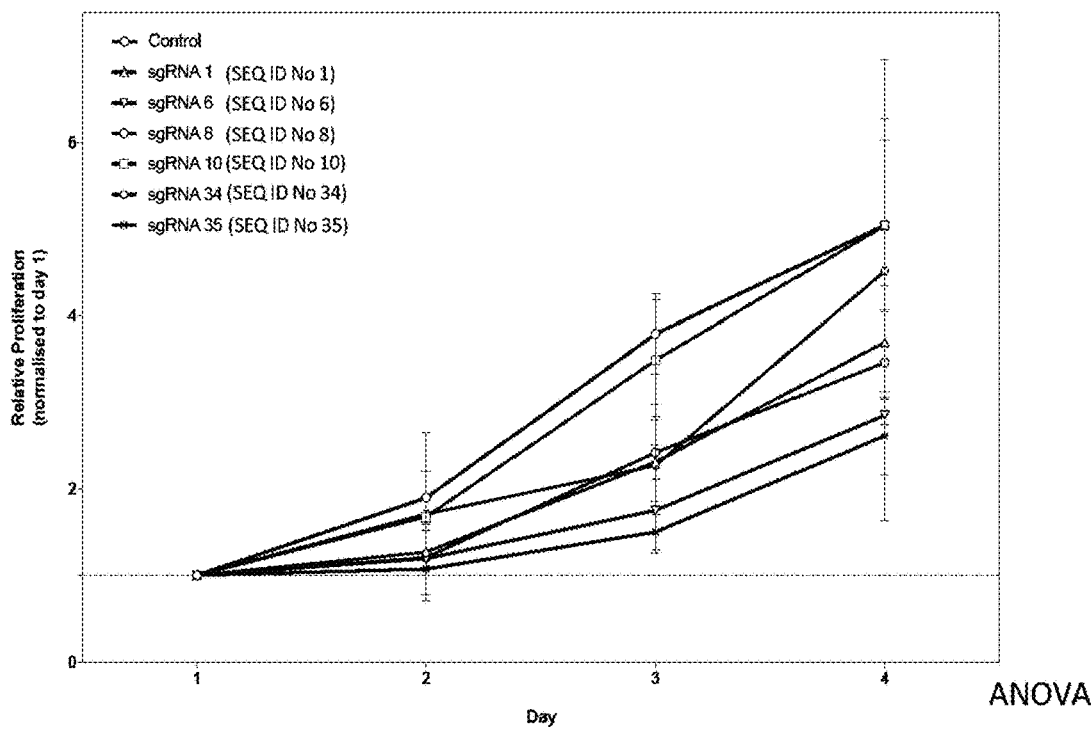
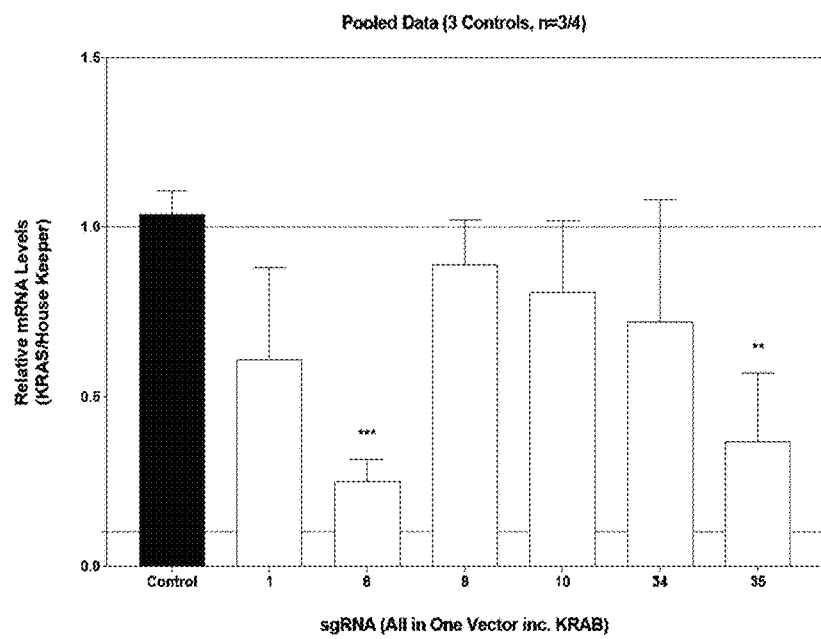

Figure 7
PANC1 cells transplanted into Nude and NSG mice
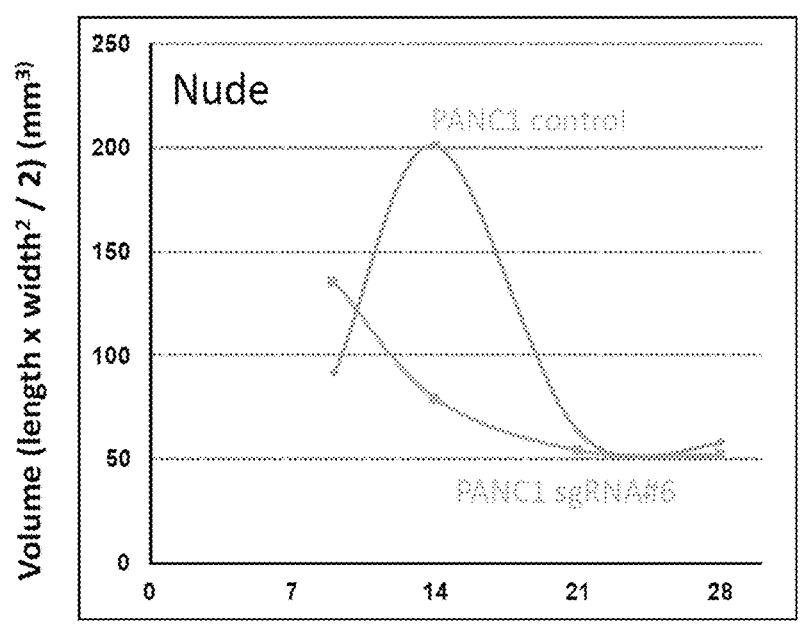
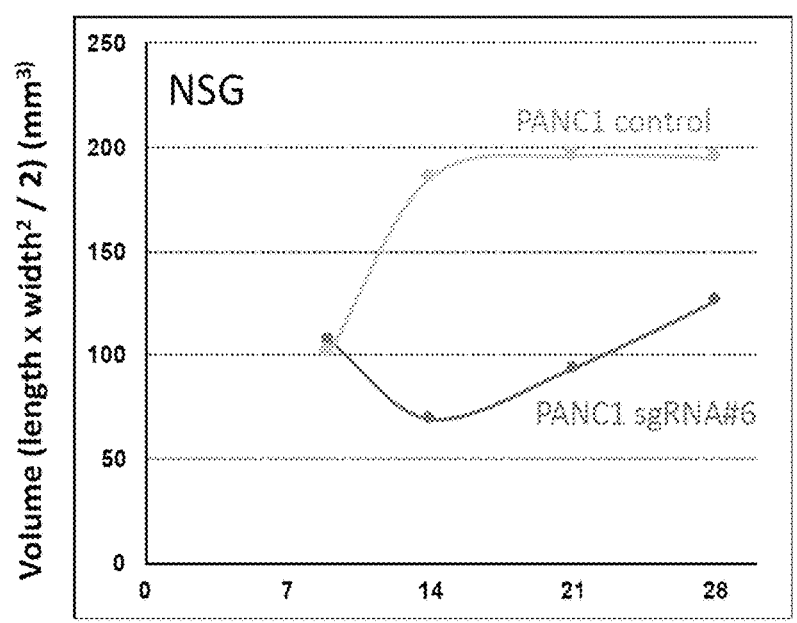

Figure 8
MiaPaca2 cells transplanted into Nude and NSG mice
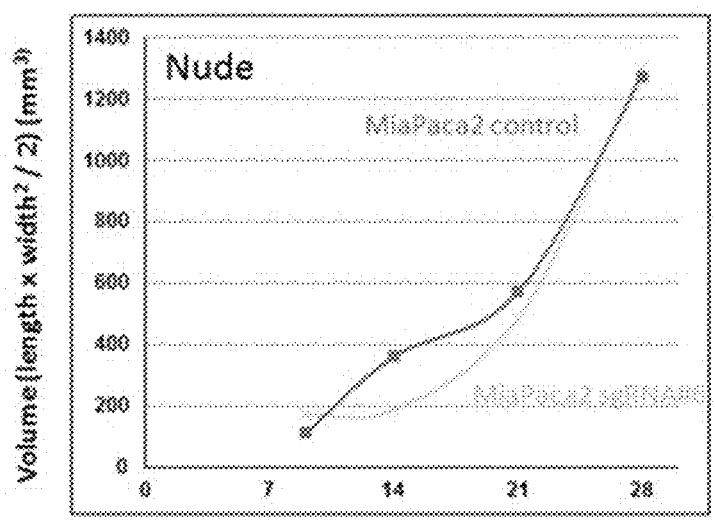
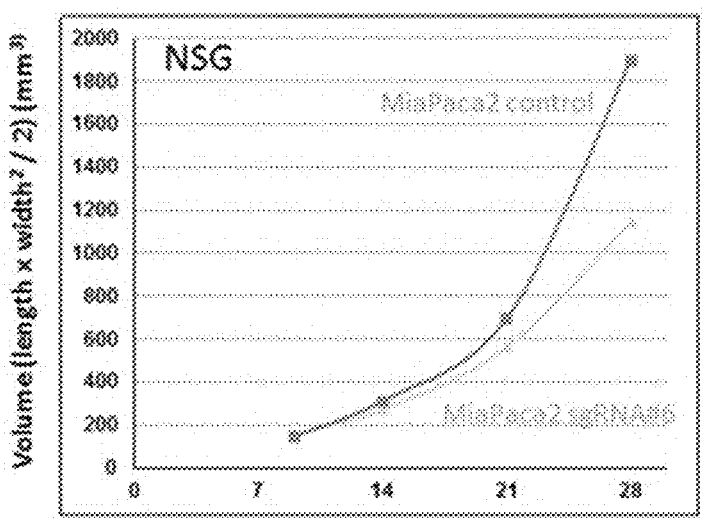

METHOD OF TREATING DISEASES ASSOCIATED WITH ELEVATED KRAS EXPRESSION USING CRISPR-GNDM SYSTEM

CROSS REFERENCE TO RELATED APPLICATIONS

This application is a 371 of International Patent Application No. PCT/JP2018/004277, filed on Feb. 7, 2018, and claims priority to U.S. Provisional Patent Application No. 62/455,845, filed on Feb. 7, 2017, and U.S. Provisional Patent Application No. 62/626,232, filed on Feb. 5, 2018, all of which are incorporated herein by reference in their entireties.

TECHNICAL FIELD

The present invention relates to a CRISPR-Guide Nucleotide Guided Modulation (GNDM) system for targeting KRAS gene and suppressing its expression, and a method of treating diseases associated with elevated KRAS activity and/or expression such as cancer using the CRISPR-GNDM system.

BACKGROUND ART

KRAS belongs to the RAS family of proteins with a molecular weight of about 21 kDa and GTP hydrolytic activity. KRAS is found inside the cell membrane, and has a role to transmit signals into cells in response to the binding of extracellular growth factors such as Epidermal Growth Factor (EGF) with the receptors. Activating mutations can be found in KRAS, and they are found in about 20% of human cancer. The frequency of the occurrence of KRAS activating mutations is high particularly in pancreatic cancer, colon cancer, and lung cancer (see "Cancer Res", Vol. 72, p. 2457, 2012). There is a report that anti-epidermal growth factor receptor (EGFR) antibody drugs: cetuximab and panitumumab are ineffective in colon cancer patients with KRAS activating mutations (see "N Engl J Med", Vol. 360, p. 1408, 2009; "J Clin Oncol", Vol. 26, p. 374, 2008; "J Clin Oncol", Vol. 26, p. 1626, 2008). KRAS has been regarded as a desirable target of anticancer drugs, and there have been long-standing attempts to discover KRAS inhibitors by a low-molecular drug discovery approach (see "Cancer Biology & Therapy", Vol. 1, p. 599, 2002). However, there is no effective therapeutic agent for treating a cancer etc. that targets the KRAS.

SUMMARY OF THE INVENTION

The present inventors found that diseases associated with elevated KRAS activity and/or expression including cancer can be treated by suppressing KRAS expression in the subject by targeting an expression regulatory region of KRAS gene using a CRISPR-GNDM system. To be specific, the present inventors found that KRAS gene expression can be efficiently suppressed by targeting a specific expression regulatory region adjacent to the transcription start site (TSS) of KRAS gene to recruit dCas9/dCpf1 to said region.

Accordingly, the present invention provides:

[1] A method of treating a disease associated with elevated KRAS activity or expression in a subject, comprising suppressing KRAS expression in the subject by targeting an expression regulatory region of KRAS gene using a CRISPR-Guide Nucleotide Directed Modulation (GNDM) system.

[2] The method of [1] above, wherein the disease is a cancer.

[3] The method of [1] above, wherein the disease is a pancreatic cancer, a lung cancer or a colorectal cancer.

[4] The method of [1] above, wherein the disease is a pancreatic cancer.

[5] The method of [4] above, wherein the pancreatic cancer is a pancreatic ductal adenocarcinoma.

[6] A CRISPR-GNDM system for suppressing KRAS expression comprising (a) a protein selected from the group consisting of dCas9 or dCpf1, a fusion protein of dCas9 or dCpf1 and Kruppel associated box (KRAB), and (b) a guide nucleotide (gN) targeting an expression regulatory region of KRAS gene.

[7] The CRISPR-dCas9 system of [6] above, wherein the expression regulatory region of KRAS gene is a region having the nucleotide sequence shown by SEQ ID NO: 65.

[8] The CRISPR-dCas9 system of [6] above, wherein the expression regulatory region of KRAS gene is a region having the nucleotide sequence at positions 81-545, preferably 134-532, of SEQ ID NO: 65.

[9] The CRISPR-dCas9 system of [6] above, wherein the gN comprises a nucleotide sequence represented by SEQ ID NO:1, 2, 6, 8, 9, 10, 23, 24, 31, 32, 34 or 35.

[10] The CRISPR-dCas9 system of [6] above, wherein the gN comprises a nucleotide sequence represented by SEQ ID NO: 1, 6, 8, 10, 23, 24, 31, 32, 34 or 35.

[11] The CRISPR-dCas9 system of [6] above, wherein the gN comprises a nucleotide sequence represented by SEQ ID NO: 6, 8, 34 or 35.

[12] The CRISPR-dCas9 system of any one of [5]-[11] above, wherein the gN comprises a sequence complementary to the expression regulatory region of KRAS gene and consisting of [20]-[24] nucleotides.

[13] The CRISPR-dCas9 system of [12] above, wherein the sequence complementary to the expression regulatory region of KRAS gene consists of 20 nucleotides.

[14] The method of any one of [1]-[5] above, wherein the CRISPR-GNDM system is the system of any one of [6]-[13] above.

[15] A method of suppressing proliferation of a cell, comprising suppressing KRAS expression in the cell by targeting an expression regulatory region of KRAS gene using a CRISPR-Guide Nucleotide Directed Modulation (GNDM) system.

[16] The method of [15] above, wherein the CRISPR-GNDM system is the system of any one of [6]-[13] above.

Effect of the Invention

The present invention can provide an effective therapeutic means for a cancer with KRAS mutation in which known drugs are ineffective.

1-10) in 24-well plate. The transfected cells were harvested on day 4 and the total RNA was isolated using Qiagen Rneasy kit. The expression level of the KRAS gene was normalized by the expression of HPRT gene in each sample. The effect of suppression by dCas9 or dCas9-KRAB was shown for each gN relative to no effector (sgRNA only) samples. Experiments were repeated three times and the average and SD were shown.

Figure 3:
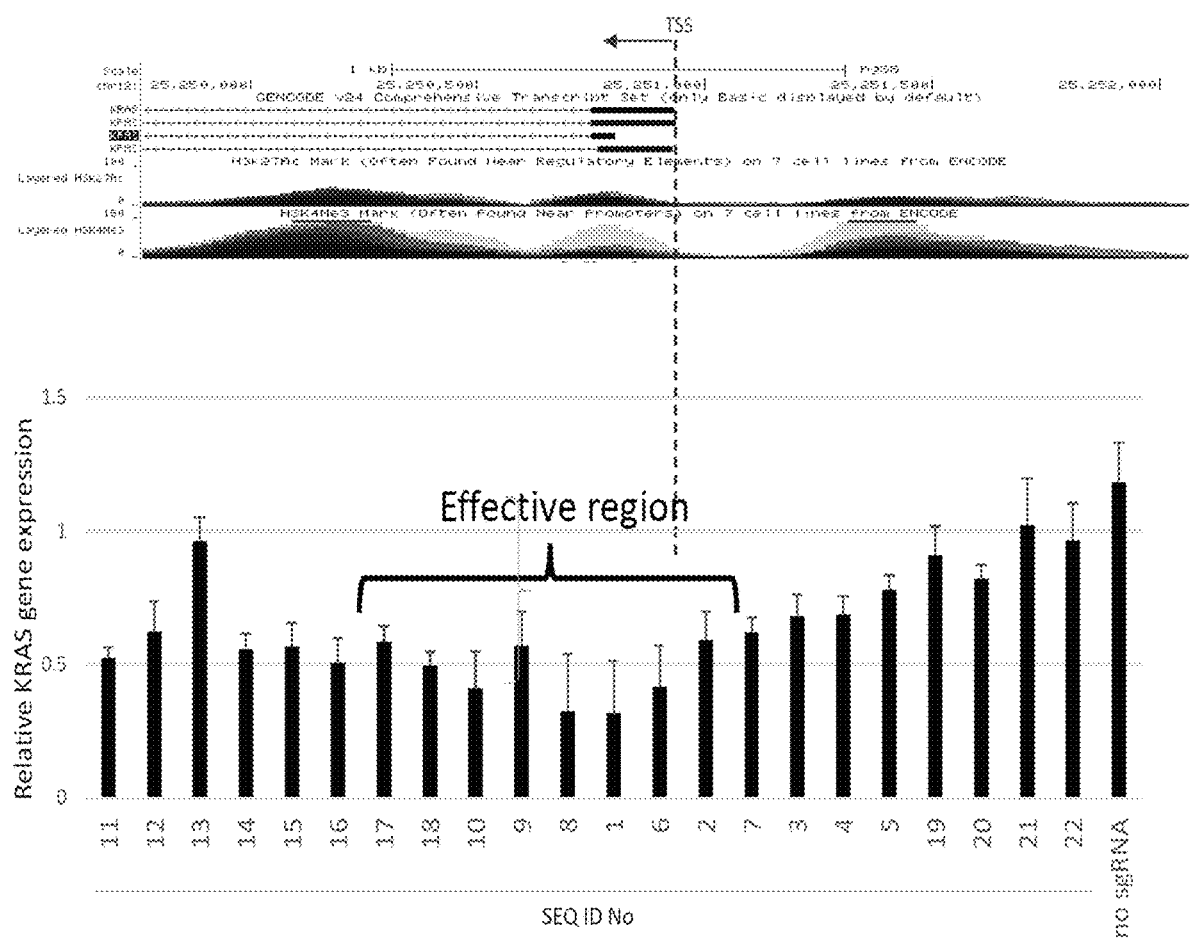

FIG. 3 shows KRAS gene suppression by dCas9-KRAB fusion protein. HEK293FT cells were co-transfected with 250 ng of CP-LvdCas9-KRAB-09 plasmid and 250 ng of the pCRISPR-LvSG03 gN expressing plasmids (SEQ ID NOs: 1-22) in 24-well plate. The transfected cells were harvested on day 4 and the total RNA was isolated using Qiagen Rneasy kit. The expression level of the KRAS gene was normalized by the expression of HPRT gene in each sample. The effect of suppression by dCas9-KRAB was shown for each gN relative to no effector (sgRNA only) samples. Experiments were repeated three times and the average and SD were shown.

Figure 4:
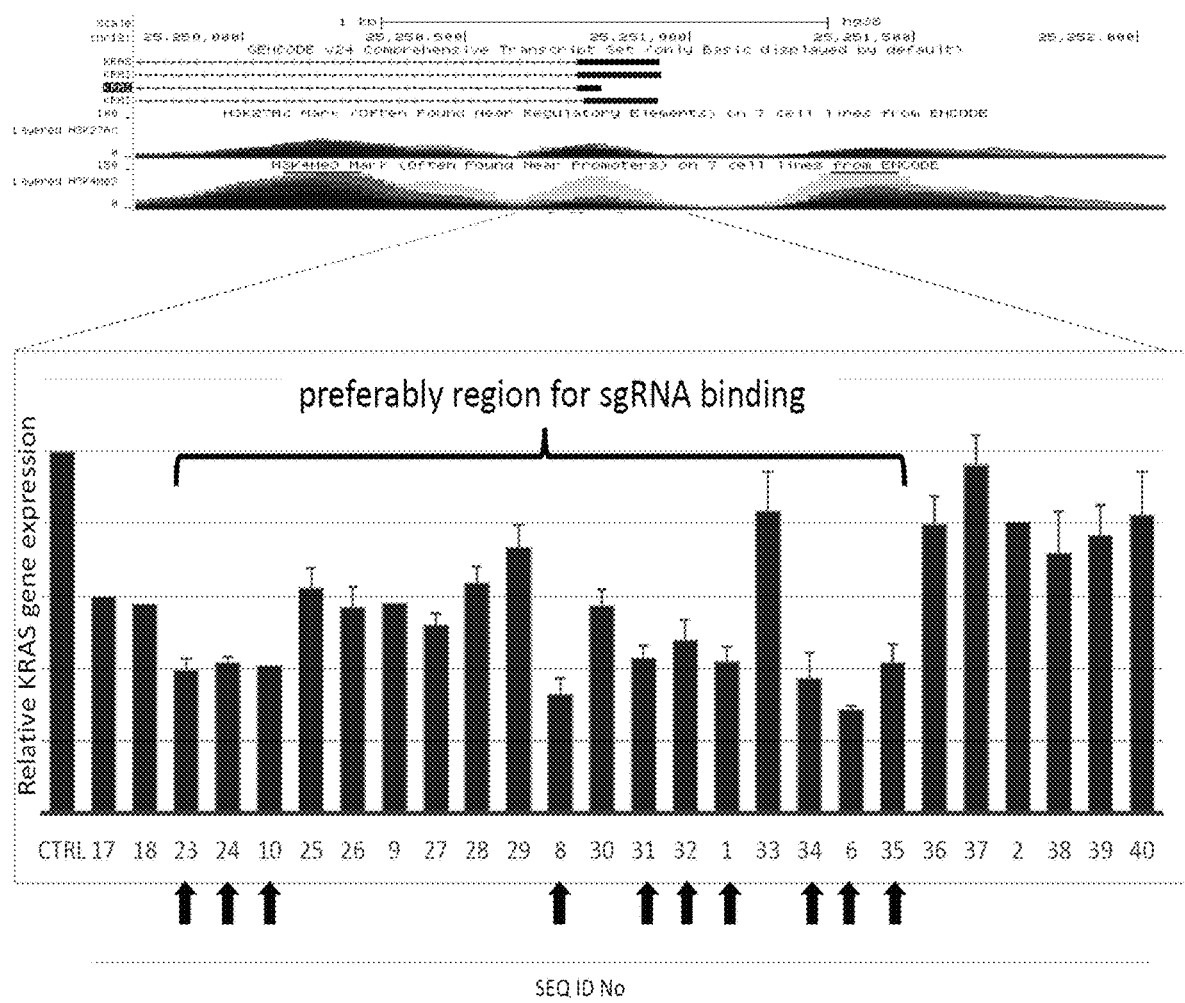

FIG. 4 shows KRAS gene suppression by dCas9-KRAB fusion protein and sgRNA expressing plasmids (SEQ ID NOs: 23-40).

FIG. 5 shows suppression of cell proliferation of PANC1 cells stably expressing dCas9-KRAB and sgRNAs in vitro. PANC1 cells were transduced with dCas9-KRAB and sgRNAs (No. 1, 6, 8, 10, 34, 35), and selected for stably expressing populations. The cell proliferation assay was done using Dojindo cell proliferation assay kit and shown as relative proliferation normalized to the values of day 1.

FIG. 6 shows suppression of cell proliferation of MiaPaca2 cells stably expressing dCas9-KRAB and sgRNAs in vitro. MiaPaca2 cells were transduced with dCas9-KRAB and sgRNAs (No. 1, 6, 8, 10, 34, 35), and selected for stably expressing populations. The cell proliferation assay was done using Dojindo cell proliferation assay kit and shown as relative proliferation normalized to the values of day 1.

FIG. 7 shows suppression of tumor growth of PANC1 cells stably expressing dCas9-KRAB and sgRNA #6 (SEQ ID NO: 6) in vivo. $1 \times 10^7$ of PANC1 stable cells or WT PANC1 cells were injected into the flank of Nude mice and NSG mice. The tumor size was measured for 28 days and the inferred tumor volume was plotted. Tumors expressing dCas9-KRAB and sgRNA #6 showed slower growth than the WT parent PANC1 cells.

FIG. 8 shows suppression of tumor growth of MiaPaca2 cells stably expressing dCas9-KRAB and sgRNA #6 in vivo. $1 \times 10^7$ of MiaPaca2 stable cells or WT MiaPaca2 cells were injected into the flank of Nude mice and NSG mice. The tumor size was measured for 28 days and the inferred tumor volume was plotted. Tumors expressing dCas9-KRAB and sgRNA #6 showed slower growth than the WT parent MiaPaca2 cells.

DESCRIPTION OF EMBODIMENTS

As used herein, the singular forms "a", "an" and "the" are intended to include both the singular and plural forms, unless the language explicitly indicates otherwise with words like "only," "single," and/or "one." It will be further understood that the terms "comprises", "comprising,", "includes" and/or "including", when used herein, specify the presence of stated features, steps, operations, elements, ideas, and/or components, but do not themselves preclude the presence or addition of one or more other features, steps, operations, elements, components, ideas, and/or groups thereof.

The present invention provides a method of treating a disease associated with elevated KRAS activity and/or expression in a subject, comprising suppressing KRAS expression in the subject by targeting an expression regulatory region of KRAS gene using a CRISPR-Guide Nucleotide Directed Modulation (GNDM) system (hereinafter also referred to as "the method of the present invention").

1. Treatment Method of the Present Invention

<<Diseases Associated with Elevated KRAS Activity and/or Expression>>

The diseases to be treated by the method of the present invention are any diseases onset by elevated KRAS activity and/or expression, which include, for example, a solid or fluid tumor, pancreatic cancer (e.g., pancreatic ductal adenocarcinoma), adenocarcinoma (e.g., pancreatic ductal adenocarcinoma, lung adenocarcinoma, etc.), colorectal cancer, progressive and/or metastatic colorectal cancer, colon cancer, lung cancer, non-small cell lung cancer, bladder cancer, brain tumor, breast cancer, cervical cancer, endometriosis, gastric cancer, head and neck cancer, kidney cancer, leukemia, myelodysplasia syndrome, myeloid leukemia, liver cancer, melanoma, ovarian cancer, prostate cancer, testicular cancer, thyroid cancer, cardiofacio-cutaneous (CFC) syndrome, Noonan syndrome, and but are not limited thereto, preferably a pancreatic, lung or colorectal cancer, more preferably a pancreatic cancer, even more preferably a pancreatic ductal adenocarcinoma.

<<Crispr-GNDM System>>

According to the present invention, the expression of normal and mutated KRAS genes can be sufficiently suppressed by recruiting a mutant Cas9 or Cpf1 that lacks double-stranded DNA break (DSB) activity (hereinafter also referred to as "dCas9" or "dCpf1", or collectively "dCas9/dCpf1") to an expression regulatory region of KRAS gene, using CRISPR-GNDM system. The "expression regulatory region of KRAS gene" as described herein may be any region of KRAS gene as long as the expression of KRAS gene can be suppressed as a result that dCas9/dCpf1 (and/or a transcription repressor bound therewith) is recruited thereto. Such region includes the promoter region and enhancer regions of KRAS gene.

Recruiting the "dCas9/dCpf1" to the expression regulatory region of KRAS gene is carried out by introducing a guide nucleotide (gN) that targets said region into a diseased cell. Accordingly, in another embodiment, the present invention provides a CRISPR-dCas9/dCpf1 system that suppresses KRAS expression, designed so as to target an expression regulatory region of KRAS gene (hereinafter also referred to as the "CRISPR-GNDM system of the present invention").

The "CRISPR-GNDM system" described herein means a system comprising (a) a class 2 CRISPR effector protein (e.g., dCas9 or dCpf1) or a complex of said CRISPR effector protein and a transcription regulator (e.g., transcription activators such as VP64, transcription repressors such as Kruppel associated box (KRAB)), and (b) a guide nucleotide (gN) that is complementary to a sequence of an expression regulatory region of a target gene, which allows recruiting the CRISPR effector protein (and the transcription regulator bound therewith) to the expression regulatory region of the target gene, thereby permitting transcriptional control of the target gene via the CRISPR effector protein per se and/or the transcription regulator. A method for controlling expression of a target gene by using a CRISPR-GNDM system is known (e.g., WO 2014/093655, WO 2014/197568, WO 2015/089486), and the descriptions of these references can be referred to. Since the CRISPR-GNDM system recognizes the object double stranded DNA sequence by a guide RNA containing a sequence complementary to the target nucleotide sequence and recruits the CRISPR effector (and the transcription repressor bound therewith), any sequence can be targeted by simply designing an oligonucleic acid capable of specifically hybridizing to the target nucleotide sequence.

The CRISPR effector protein to be used in the present invention is not particularly limited as long as it belongs to the class 2 CRISPR system, and preferred is Cas9 or Cpf1. Examples of Cas9 include, but are not limited to, *Streptococcus pyogenes*-derived Cas9 (SpCas9; PAM sequence NGG (N is A, G, T or C. The same shall apply hereinafter.), *Streptococcus thermophilus*-derived Cas9 (StCas9; PAM sequence NNAGAAW (W is A or T. The same shall apply hereinafter), *Neisseria meningitides*-derived Cas9 (MmCas9; PAM sequence NNNNGATT), *Streptococcus aureus*-derived Cas9 (SaCas9; PAM sequence NNGRRT) and the like. Examples of Cpf1 include, but are not limited to, Lachnospiraceae bacterium-derived Cpf1 (LbCpf1; PAM sequence TTTN), *Francisella novicida*-derived Cpf1 (FnCpf1; PAM sequence TTN), *Acidaminococcus* sp.-derived Cpf1 (AsCpf1; PAM sequence TTTN) and the like.

Preferably, Cas9 is SpCas9 that is less limited by PAM (since SpCas9 PAM is defined by substantially 2 nucleotides (i.e., GG), theoretically, SpCas9 can target almost any position of genome). AS a dCas9 to be used in the present invention, any of Cas9 wherein the cleavage ability of the both chains of the double stranded DNA is inactivated can be used. For example, in the case of SpCas9, a double mutant of D10A, wherein the 10th Asp residue is converted to an Ala residue and lacking cleavage ability of a chain opposite to the chain forming a complementary chain with a guide RNA, and H840A, wherein the 840th His residue is converted to an Ala residue and lacking cleavage ability of chain complementary to guide RNA, can be used, and other dCas9 can be used similarly. On the other hand, in the case of Cpf1, while preferred is FnCpf1 that is less limited by PAM (since FnCpf1 PAM is defined by substantially 2 nucleotides (i.e., TT), theoretically, FnCpf1 can target almost any position of genome), LbCpf1 and AsCpf1 whose PAMs are defined by substantially 3 nucleotides (i.e., TTT) are also preferable. AS a dCpf1 to be used in the present invention, any of Cpf1 wherein the cleavage ability of the both chains of the double stranded DNA is inactivated can be used. For example, in the case of FnCpf1, D917A, E1006A or D1255A, in the case of AsCpf1, D908A, E993A or D1263A, and in the case of LbCpf1, D832A, E925A, D947A or D1180A can be used, respectively.

As described above, while the CRISPR effector protein such as dCas9/dCpf1 recruited to the expression regulatory region of KRAS gene via the gN can suppress KRAS expression without co-existence of a transcription repressor, by preventing binding of an endogenous transacting factor, a transcription repressor such as Kruppel associated box (KRAB) motif can be further used in combination with the CRISPR effector protein. In such case, the expression of KRAS gene can be more potently suppressed by recruiting a complex of the CRISPR effector and the transcription repressor to the expression regulatory region.

The term "transcription repressor" described herein means a protein or a domain thereof having an activity that suppresses transcription of a target gene.

The transcription repressor to be used in the present invention is not limited as long as it can suppress the expression of KRAS gene, for example, includes Kruppel associated box (KRAB), MBD2B, v-ErbA, SID (including a concatemer of SID (SID4X)), MBD2, MBD3, DNMT family (e.g., DNMT1, DNMT3A, DNMT3B), Rb, MeCP2, ROM2, LSD1 and AtHD2A. Preferred is KRAB.

The transcription repressor can be originated from any organism as long as it can suppress the expression of KRAS gene. For example, transcription repressors originated from vertebrates (e.g., mammals such as human, porcine, bovine, canine and chimpanzee, Ayes such as chicken and the like), preferably mammals, more preferably human, can be used.

As mentioned above, in a preferable embodiment, KRAB is used as the transcription repressor. KRAB is a category of transcriptional repression domains present in approximately 400 human zinc finger protein-based transcription factors (KRAB-ZFPs). The KRAB domain typically consists of about 75 amino acid residues, while the minimal repression module is approximately 45 amino acid residues (Proc. Natl. Acad. Sci. U.S.A. 91(10): 4509-13, 1994). Since human genes encoding KRAB-ZFPs include KOX1/ZNF10, KOX8/ZNF708, ZNF43, ZNF184, ZNF91, HPF4, HTF10 and HTF34, the KRAB domain to be used in the present invention can be cloned from these genes.

In one embodiment, a complex of the CRISPR effector protein (dCas9/dCpf1) and the transcription repressor can be provided in the form of a fused protein. In this case, the KRAB domain can be fused with either N-terminus or C-terminus of the CRISPR effector protein. The resulting dCas9/dCpf1-KRAB protein is recruited to an expression regulatory region within the KRAS gene (e.g. promoter or enhancer region) via interaction with a gN containing a nucleotide sequence complementary to the target expression regulatory region and thereby exerts its transcriptional repressor effect.

In another embodiment, a protein-binding domain such as SH3 domain, PDZ domain, GK domain, GB domain and the like and a binding partner thereof may be fused with the CRISPR effector protein such as dCas9/dCpf1 and the transcription repressor, respectively, and provided as a protein complex via an interaction of the domain and a binding partner thereof. In another embodiment, the CRISPR effector protein and the transcription repressor may be each fused with intein, and they can be linked by ligation after protein synthesis. The CRISPR effector protein and the transcription repressor can also be bound by utilizing an RNA aptamer such as MS2F6, PP7 and the like and an RNA scaffold constructed by a protein binding to said aptamer. Preferably, one or more nuclear localization signals (NLS) are ligated to the N- and/or C-termini of the CRISPR effector protein, in order to facilitate nuclear transition thereof. When the transcription repressor is used in combination with the CRISPR effector protein, NLS can also be ligated to both or either of N- and C-termini of the transcription repressor. In addition, a tag such as hemagglutinin (HA), fluorescent protein (e.g., GFP) can be bound to the CRISPR effector protein and/or the transcription repressor.

The second element of the CRISPR-GNDM system of the present invention is a guide nucleotide (gN) that contains a nucleotide sequence (hereinafter also referred to as "targeting sequence") complementary to the nucleotide sequence adjacent to PAM of the target strand in the expression regulatory region of KRAS gene. When the CRISPR effector protein is dCas9, the gN is provided as a chimeric nucleotide of truncated crRNA and tracrRNA (i.e., single guide RNA (sgRNA)), or combination of separate crRNA and tracrRNA. The gN may be provided in a form of RNA, DNA or DNA/RNA chimera. Thus, hereinafter, as long as technically possible, the terms "sgRNA", "crRNA" and "tracrRNA" are used to also include the corresponding DNA and DNA/RNA chimera in the context of the present invention. The crRNA contains the targeting sequence. The targeting sequence is not limited as long as it can specifically hybridize with the target strand at an expression regulatory region of KRAS gene and recruit the CRISPR effector protein (and a transcription repressor bound therewith) to the expression regulatory region. For example, when SpdCas9 is used as the CRISPR effector protein, the targeting sequences listed in Table 1 are exemplified. In Table 1, while targeting sequences consisting of 20 nucleotides are described, the length of targeting sequence can be arbitrarily chosen in the range of 18-25 nucleotides, more preferably 20-24 nucleotides. When SpdCas9 is used as the CRISPR effector protein, the gN to be used in the present invention preferably contains the nucleotide sequences represented by SEQ ID NO: 1, 2, 6, 8, 9, 10, 23, 24, 31, 32, 34 or 35, more preferably SEQ ID NO: 1, 6, 8, 10, 23, 24, 31, 32, 34 or 35, further more preferably SEQ ID NO: 6, 8, 34 or 35 as a targeting sequence. A crRNA containing a targeting sequence other than those listed in Table 1 can be designed and produced based on the nucleotide sequence information of KRAS gene. When SadCas9 or LddCpf1/AsCpf1 that recognizes a different PAM is used as the CRISPR effector protein, targeting sequences can be designed and produced in the same manner. Examples of targeting sequences for SadCas9 and LddCpf1/AsdCpf1 include, but are not limited to, those listed in Table 2 and Table 3, respectively. In Tables 1-3, the sequences are indicated as DNA sequences. When an RNA is used as the gN, "T" should be read "U" in each sequence.

TABLE 1

| SEQ ID NO. | Position | Strand | Sequence | PAM | Specificity Score | Efficiency Score |
| --- | --- | --- | --- | --- | --- | --- |
| 1 | 25403769 | 1 | TCGCTCCCAGTCCGAAATGG | CGG | 89.4 | 57.4 |
| 2 | 25403862 | -1 | CGGAGCTCGATTTTCCTAGG | CGG | 83.2 | 64.9 |
| 3 | 25403968 | 1 | CTTCAGACGGGCGTACGAGA | GGG | 98.3 | 60.2 |
| 4 | 25404183 | 1 | GAGGGACTGCCGGACCCACG | CGG | 80.2 | 63.7 |
| 5 | 25404237 | -1 | GTCCCGCTCCGGGTCAGAAT | TGG | 91.0 | 37.7 |
| 6 | 25403808 | -1 | GGCAGTGGCGGCGGCGAAGG | TGG | 48.6 | 45.8 |
| 7 | 25403914 | -1 | ATCGATAGCTCTGCCCTCTG | CGG | 39.9 | 59.8 |
| 8 | 25403680 | -1 | TGCGGGAGAGAGGTACGGAG | CGG | 41.9 | 68.4 |
| 9 | 25403586 | -1 | AATGAATTAGGGGTCCCCGG | AGG | 84.2 | 68.8 |
| 10 | 25403482 | -1 | CGCGGGGAGTGAGGAATGGG | CGG | 28.9 | 63.1 |
| 11 | 25249767 | 1 | GGTAGTATAAAAGAGACGAG | GGG | 74.8 | 70.7 |
| 12 | 25249866 | 1 | CTGTCTACACTCAACTAGCA | AGG | 73.8 | 63.2 |
| 13 | 25249939 | -1 | AGGAAAAAGTTAATCCCAGA | TGG | 51.1 | 61.0 |
| 14 | 25250037 | -1 | TGACATTGCTGTGGCCACAA | AGG | 47.7 | 64.8 |
| 15 | 25250179 | -1 | GGATGTGTGAGTAAGAGGGG | AGG | 48.4 | 65.4 |
| 16 | 25250280 | 1 | TAGAGATGCCAAATGCAGCA | GGG | 54.8 | 67.4 |
| 17 | 25250374 | -1 | TGCGGTGGAGGTTACTCCCG | CGG | 92.5 | 60.3 |
| 18 | 25250454 | -1 | TTCCTCCTCCCCGAGAGCCG | CGG | 68.6 | 64.8 |
| 19 | 25251399 | -1 | TGCTCTTCGCAGCTTCTCTG | TGG | 49.1 | 55.9 |
| 20 | 25251553 | 1 | GCGGACGATTTCCCACACCG | GGG | 95.5 | 74.3 |
| 21 | 25251716 | 1 | GATATTTTGAACCCATCACA | AGG | 61.8 | 66.8 |
| 22 | 25251891 | 1 | AGTTAAGACATTAAACAATG | GGG | 48.0 | 72.1 |
| 23 | 25250501 | 1 | CGTCCAGGAAGCAGCACCAG | CGG | 31.1 | 60.8 |
| 24 | 25250531 | -1 | GGGCGGTGCGGGGCTGAGGA | GGG | 26.3 | 50.3 |
| 25 | 25250557 | -1 | ACGCGGCGGCGCGGGGAGTG | AGG | 32.7 | 47.9 |
| 26 | 25250593 | -1 | CTGGGTGAGAGGGGTCTGCA | GGG | 45.0 | 49.7 |
| 27 | 25250662 | -1 | GCGGCGAGTGAATGAATTAG | GGG | 43.5 | 66.6 |
| 28 | 25250713 | 1 | GGCAAAGAGGGTCGGGACCC | GGG | 41.1 | 48.0 |

TABLE 1-continued

| SEQ ID NO. | Position | Strand | Sequence | PAM | Specificity Score | Efficiency Score |
|---|---|---|---|---|---|---|
| 29 | 25250731 | -1 | CGGAGCGGACCACCCCTCCT | GGG | 42.9 | 50.3 |
| 30 | 25250769 | -1 | CCAGAGGCTCAGCGGCTCCC | AGG | 36.9 | 43.0 |
| 31 | 25250792 | -1 | AGGCACTGAAGGCGGCGGCG | GGG | 32.0 | 48.2 |
| 32 | 25250812 | -1 | ACTGGGAGCGAGCGCGGCGC | AGG | 42.2 | 42.3 |
| 33 | 25250843 | 1 | AGTCCGAAATGGCGGGGGCC | GGG | 42.2 | 44.4 |
| 34 | 25250850 | -1 | GGCGGCTCGGCCAGTACTCC | CGG | 76.3 | 37.9 |
| 35 | 25250886 | -1 | AGCAGCGGCGGCGGCAGTGG | CGG | 32.5 | 41.0 |
| 36 | 25250913 | 1 | CGCTGCTGCCTCCGCCGCCG | CGG | 34.7 | 50.2 |
| 37 | 25250919 | -1 | ATTTTCCTAGGCGGCGGCCG | CGG | 84.6 | 51.2 |
| 38 | 25251055 | 2 | GGAGCGGCTGAGGGCGGTGT | GGG | 60.4 | 51.9 |
| 39 | 25251069 | 1 | CGGTGTGGGAAGAGGGAAGA | GGG | 28.2 | 46.6 |
| 40 | 25251087 | 1 | GAGGGGGAGGCAGCGAGCGC | CGG | 53.5 | 41.1 |

TABLE 2

| SEQ ID NO | Position | Strand | Sequence | PAM | Specificity Score | Efficiency Score |
|---|---|---|---|---|---|---|
| 41 | 25403777 | 1 | CCAGTCCGAAATGGCGGGGCC | GGCAGT | 88.3 | 2.9 |
| 42 | 25403885 | 1 | AAATCGAGCTCCGAGCACACCG | ATGAGT | 96.1 | 76.7 |
| 43 | 25403954 | -1 | CCTCTCGTACGCCCGTCTGAAC | AAGAAT | 97.5 | 25.8 |
| 44 | 25404088 | 1 | CGGGGGCCGGGCCGGCGGAGGA | AGGGGT | 47.3 | 0.2 |
| 45 | 25404107 | 1 | GGAAGGGGTGGCTGGCGCGGTC | TAGGGT | 72.2 | 0.1 |
| 46 | 25404135 | 1 | GGCGAGCCGGGCCGGCTGGAGA | GCGGGT | 65.5 | 2.7 |
| 47 | 25404188 | -1 | TAGGCAGGGGCGGGCCGCCGC | GTGGGT | 58.8 | 0.3 |
| 48 | 25404243 | -1 | GCGGTCCGGTCCCGCTCCGGGT | CAGAAT | 84.9 | 31.0 |
| 49 | 25404249 | -1 | CCCGCCGCGGTCCGGTCCCGCT | CCGGCT | 94.5 | 6.9 |
| 50 | 25404269 | 1 | GGACCGGACCGCGGCGGGCTGT | GCGCAT | 92.9 | 0.9 |

TABLE 3

| SEQ ID NO | Position | Strand | Sequence | PAM | Specificity Score | Efficiency Score |
|---|---|---|---|---|---|---|
| 51 | 25403746 | -1 | GGACTGGGAGCGAGCGCGGCGCA | TTTC | 99.2 | NA |
| 52 | 25403845 | -1 | CTAGGCGGCGGCCGCGGCGGCGG | TTTC | 98.2 | NA |
| 53 | 25403846 | -1 | CCTAGGCGGCGGCCGCGGCGGCG | TTTT | 97.0 | NA |

As shown in the following Examples (FIG. 4), when the expression regulatory region of KRAS gene is a region including DNA sequence targeted by the targeting sequences shown by SEQ ID NO: 23 to SEQ ID NO: 35, a high suppressive effect on the KRAS gene expression was shown. Therefore, not only a gN containing any of the sequences described in Table 1 but also any gN containing a targeting sequence at least a part of which targets a sequence within such expression regulatory region is expected to show a high suppressive effect. Specifically, as such expression regulatory region of KRAS gene to be targeted, a region (545 bp) having the nucleotide sequence shown by SEQ ID NO 65, which corresponds to positions 25250371 to 25250915 of human chromosome 12 (GRCh38/h38 human genome assembly; NC_000012), can be mentioned, a region (465 bp) at positions 81-545 of SEQ ID NO: 65 is more preferable, a region (399 bp) at positions 134-532 of SEQ ID NO: 65 is even more preferable. The targeting sequences thus designed can be evaluated for its off-target activities. For initial screening of predicted off-target activities, there are a number of bioinformatics tools known and publicly available that can be used to predict the most likely off-target sites; and since binding to target sites in the CRISPR-GNDM system is driven by Watson-Crick base pairing between complementary sequences, the degree of dissimilarity (and therefore reduced potential for off-target binding) is essentially related to primary sequence differences: mismatches and bulges, i.e. bases that are changed to a non-complementary base, and insertions or deletions of bases in the potential off-target site relative to the target site. An exemplary bioinformatics tool called Benchling (https://benchling.com) and COSMID (CRISPR Off-target Sites with Mismatches, Insertions and Deletions) (available on the web at https://crispr.bme.gatech.edu) compiles such similarities.

The crRNA containing a sequence complementary to the target strand of the target nucleotide sequence can be ligated to a tracrRNA necessary for recruiting dCas9 protein to give an sgRNA. When the sgRNA is brought into contact with the subject genome, the crRNA in the sgRNA is hybridized to the target strand of the expression regulatory region of interest and tacrRNA ligated to 3'-end of the crRNA recruits dCas9 protein to recognize PAM. Alternatively, the crRNA and tracrRNA can be provided separately, and assembled in a host cells of interest to form a guide RNA (gRNA). Since the dCas9 protein is inactivated, it does not cleave the genome. Instead, due to the presence of the dCas9 protein in the expression regulatory region of KRAS gene and/or the action of the transcription repressor bound to the dCas9 protein on the expression regulatory region, the expression of KRAS gene is suppressed. On the other hand, when the CRISPR effector protein is Cpf1, the (s)gRNA can only consist of crRNA, wherein the crRNA contains a targeting sequence complementary to the target strand of the target nucleotide sequence and 5'-handle sequence ligated to 5'-end of the targeting sequence, which is necessary for recruiting dCpf1 protein to the target expression regulatory region.

In one embodiment, two or more (s)gRNAs that have different targeting sequences complementary to different expression regulatory regions of KRAS gene can be used. In this case, more potent suppressing effect on the expression of KRAS gene can be expected.

<<Nucleic Acids Encoding CRISPR-GNDM System>>

The CRISPR-GNDM system of the present invention comprising (a) a CRISPR effector protein such as dCas9/dCpf1 or a complex of the CRISPR effector protein and a transcription repressor, and (b) a gN containing a targeting sequence complementary to the target strand of an expression regulatory region within KRAS gene can be introduced into a diseased cell in an organism to be treated in the form of DNAs encoding (a) and (b) above. A DNA encoding Cas9 or Cpf1 can be cloned by, for example, synthesizing an oligoDNA primer covering CDS based on the cDNA sequence information thereof, and amplifying by the RT-PCR method using, as a template, the total RNA or mRNA fraction prepared from Cas9- or Cpf1-producing cells. A DNA encoding dCas9/dCpf1 can be obtained by introducing a mutation to convert an amino acid residue of the part important for the DNA cleavage activity (e.g., 10th Asp residue and 840th His residue for SpCas9, 908th Asp, 993rd Glu or 1263rd Asp residue for AsCpf1, though not limited thereto) to other amino acid, into the cloned DNA encoding Cas9, by a site-directed mutagenesis method known per se.

Alternatively, a DNA encoding dCas9/Cpf1 can be obtained by chemically synthesizing the DNA chain, or by connecting synthesized partly overlapping oligoDNA short chains by utilizing the PCR method and the Gibson Assembly method to construct a DNA encoding the full length thereof. The advantage of constructing a full-length DNA by chemical synthesis or a combination of PCR method or Gibson Assembly method is that the codon to be used can be designed in CDS full-length according to the host into which the DNA is introduced. In the expression of a heterologous DNA, the protein expression level is expected to increase by converting the DNA sequence thereof to a codon highly frequently used in the host organism. As the data of codon use frequency in host to be used, for example, the genetic code use frequency database (http://www.kazusa.or.jp/codon/index.html) disclosed in the home page of Kazusa DNA Research Institute can be used, or documents showing the codon usage frequency in each host may be referred to. By reference to the obtained data and the DNA sequence to be introduced, codons showing low usage frequency in the host from among those used for the DNA sequence may be converted to a codon coding the same amino acid and showing high usage frequency.

A DNA encoding a transcription repressor can also be cloned from a cell that produces the same. For example, a DNA encoding KRAB domain derived from human KOX-1 can be cloned by designing suitable primers for the upstream and downstream of coding region of said KRAB domain based on the cDNA sequence of KOX-1 (accession No. NM_015394.4) registered in the NCBI database, and cloning from human-derived mRNA fraction by the RT-PCR method. Alternatively, A DNA encoding a transcription repressor can be constructed as a DNA having codon usage suitable for expression in an organism to be introduced using chemical synthesis (optionally in combination with PCR method or Gibson Assembly method).

The cloned DNA encoding a transcription repressor can be directly, or after digestion with a restriction enzyme, or after addition of an adequate linker and/or an NLS, ligated to a DNA encoding a CRISPR effector protein to give a DNA encoding a fused protein. Alternatively, a DNA encoding a CRISPR effector protein, and a DNA encoding a transcription repressor may be each fused with a DNA encoding a binding domain or a binding partner thereof, or both DNAs may be fused with a DNA encoding an intein, whereby the CRISPR effector protein and the transcription repressor are translated in a host cell to form a complex. In these cases, a linker and/or an NLS can be linked to a suitable position of either or both of the DNAs when desired.

A DNA encoding the (s)gRNA of the present invention discussed in detail above can be chemically synthesized using a DNA/RNA synthesizer based on its sequence information. For example, a DNA encoding an (s)gRNA for dCas9 has a deoxyribonucleotide sequence encoding a crRNA containing a targeting sequence complementary to an expression regulatory region of KRAS gene and at least a part of the "repeat" region (e.g., GUUUUAGAGCUA; SEQ ID NO:54) of the native SperRNA, and a deoxyribonucleotide sequence encoding tracrRNA having at least a part of the "anti-repeat" region complementary to the repeat region of the crRNA (e.g., UAGCAAGUUAAAAU; SEQ ID NO:55) and the subsequent stem-loop 1, linker, stem-loop 2 and stem-loop 3 regions (AAGGCUAGU-CCGUUAUCAACUUGAAAAGUGGCACCGAGUCG-GUGCUU; SEQ ID NO:56) of the native SptracrRNA, optionally linked via a tetraloop (e.g., GAAA). On the other hand, a DNA encoding an gRNA for dCpf1 has a deoxyribonucleotide sequence encoding a crRNA alone, which contains a targeting sequence complementary to an expression regulatory region of KRAS gene and the preceding 5'-handle (e.g., AAUUUCUACUCUUGUAGAU; SEQ ID NO:57). When a protein other than spCas9 and Cpf1 is used as a CRISPR effector protein, a tracrRNA for the protein to be used can be designed appropriately based on a known sequence and the like. The DNA encoding the CRISPR effector protein (optionally ligated with the DNA encoding the transcription repressor) can be subcloned into an expression vector such that said DNAs are located under the control of a promoter that is functional in a host cell of interest.

As the expression vector, plasmids for expression in animal cells (e.g., pA1-11, pXT1, pRc/CMV, pRc/RSV, pcDNAI/Neo); vectors derived from animal virus such as retrovirus, vaccinia virus, adenovirus, adeno-associated virus, etc, and the like can be used. When a viral vector is used as the expression vector, a vector derived from a serotype suitable for infecting a diseased organ of interest can preferably be used. For example, in the case of adeno-associated viral (AAV) vector, when the disease to be treated is pancreatic cancer, AAV8-based vectors more likely to infect pancreas (e.g., scAAV2/8-LP1-hFIXco) can be preferred.

As the promoter, any promoter appropriate for the host cell can be used. For example, when the host is a mammalian cell, SRα promoter, SV40 promoter, LTR promoter, CMV (cytomegalovirus) promoter, RSV (Rous sarcoma virus) promoter, MoMuLV (Moloney mouse leukemia virus) LTR, HSV-TK (simple herpes virus thymidine kinase) promoter and the like are used. Of these, CMV promoter, SRα promoter and the like are preferable.

As the expression vector, besides those mentioned above, one containing enhancer, splicing signal, polyadenylation signal, a selectable marker such as drug resistance gene and the like, replication origins for mammalian cell and *E. coli* and the like on demand can be used.

The DNA encoding the (s)gRNA can also be subcloned into the expression vector mentioned above, but pol III-type promoters (e.g., SNR6, SNR52, SCR1, RPR1, U6 and H1 promoters) and terminators (e.g., $T_6$ sequence) can preferably be used. When a pol III promoter is used, a nucleotide sequence containing 4 or more T residue repeats should be avoided to use as a targeting sequence.

The DNA encoding the CRISPR effector protein or the complex of the CRISPR effector protein and the transcription repressor and the DNA encoding the (s)gRNA can be inserted into separate vectors, respectively, or into a single vector.

The gN of the CRISPR-GNDM system of the present invention can also be chemically synthesized using a DNA/RNA synthesizer, and introduced into a host cell of interest, as it is (i.e., without being inserted into a vector).

<<Introduction of CRISPR-GNDM System>>

A method of introducing the CRISPR-GNDM system of the present invention is not limited as long as the CRISPR-GNDM system can be efficiently and/or selectively delivered to a diseased site of interest. In a preferable embodiment, access for the target lesion can be carried out by in vivo injection via EUS (endoscopic ultra-sound) biopsy needle. This device is an endoscope used for gastroscopy and the like, in the distal end of which an ultrasound transducer is integrated. For example, in the case of pancreatic cancer, EUS is introduced through mouth and proceeded close to pancreas (i.e., stomach or duodenum), and there emits ultrasound waves to find out pancreas and a cancerous lesion therein. After the position of pancreatic cancer is identified, a biopsy needle is taken out of the tip of endoscope and inserted into the cancerous lesion. When the tip of needle reaches the center of cancerous lesion, an expression vector carrying the DNA encoding the CRISPR-GNDM system (i.e., dCas9/dCpf1 or a complex of dCas9/dCpf1 and transcription repressor, and (s)gRNA that targets an expression regulatory region of KRAS gene) is injected from the needle (in the case of a viral vector such as AAV, the vector is administered in an amount of $1-10 \times 10^{12}$ viral genome (vg)/kg). As mentioned above, gN cen also be introduced without inserting into an expression vector. For diseases other than pancreatic cancer, EUS-guided fine needle injection methods established for various target organs can also be used.

In another embodiment, (1) a non-viral expression vector carrying the DNA encoding the CRISPR effector protein or the complex of the CRISPR effector protein and the transcription repressor, and (2)(a) a non-viral expression vector carrying the DNA encoding the (s)gRNA or (b) the gN per se. can be introduced into cancerous lesion of interest using biologically compatible nanoparticles.

The biologically compatible nanoparticles in which the DNA encoding the CRISPR-GNDM system include, but are not limited to, polylactic acid (PLA), polyglycolic acid (PGA), lactic acid-glycolic acid copolymer (PLGA), poly-ε-caprolactone, poly-β-hydroxybutyric acid and the like. Preferred is PLA, PGA, PLGA and the like, more preferably PLGA. A preparation containing the DNA and the biologically compatible nanoparticles, for example, can be formulated according to the method described in JP 2011-111429 A. To be specific, this method comprises a step of providing the biologically compatible nanoparticles as a solution containing the same, and a step of distilling a good solvent away from the solution to give a suspension of the nanoparticles. The biologically compatible nanoparticle has a molecular weight preferably in the range of 5,000-200,000, more preferably in the range of 15,000-25,000. When the biologically compatible nanoparticle is PLGA, the ratio of lactic acid to glycolic acid may be 1:99 to 99:1. The particle size of the biologically compatible nanoparticle is not limited as long as the biologically compatible nanoparticle can deliver the DNA contained therein to a diseased site of interest and introduce the same into the target cells (thereby suppressing the expression of KRAS gene in the target cells). For example, the particle size is preferably 500 nm or less, more preferably 300 nm or less, as the mean diameter in the final preparation. The content of the DNA in the preparation is typically 0.5 or more % by weight and 30 or less % by weight. Since a plasma membrane in a living body is negatively charged, adhesiveness of the nanoparticle against the plasma membrane can be increased to improve internalization efficiency of the nanoparticle, by subjecting the surface of the nanoparticle to a ξ potential using a cationic polymer.

The preparation of the DNA encoding the CRISPR-GNDM system-capsulated nanoparticles can also be introduced into the target diseased site using EUS-guided fine needle injection as mentioned above.

The suppression efficiency of KRAS gene expression of the CRISPR-GNDM system of the present invention can be evaluated, for example, by introducing the DNA encoding the CRISPR-GNDM system into a human cell in vitro, culturing the human cell for a certain period and determine an amount of KRAS mRNA or KRAS protein in the human cell by a method known per se.

2. Suppression Method of the Present Invention

The present invention also provides a method of suppressing proliferation of a cell, comprising suppressing KRAS expression in the cell by targeting an expression regulatory region of KRAS gene using above-mentioned CRISPR-GNDM system.

3. Pharmaceutical of the Present Invention

The present invention also provides a pharmaceutical comprising the nucleic acid mentioned above (including an expression vector containing the same) (hereinafter referred to as the "pharmaceutical of the present invention"). The pharmaceutical of the present invention can be used for the treatment of diseases associated with elevated activity and/or expression of KRAS. The diseases associated with elevated activity and/or expression of KRAS are as described above. In addition, the pharmaceutical of the present invention can be used for the suppression of proliferation of cells including cancer cells. Examples of the cancer to be the derivation of the cell include the aforementioned cancers.

The active ingredient of the pharmaceutical of the present invention, the CRISPR-GNDM system alone, or in combination with suitable additives conventionally used in the art, can be formulated into the pharmaceutical. The CRISPR-GNDM system is preferably used in the form of nucleic acid, more preferably in the form of expression vector carrying the DNA encoding the CRISPR-GDNM system. Said expression vector may be a viral vector or a non-viral vector. In the case of viral vector, said vector can be prepared as a viral particle encapsulating the DNA encoding the CRISPR-GNDM system therein. In the case of non-viral vector, said vector can be provided in the form that is encapsulated in a biologically compatible nanoparticle.

The pharmaceutical of the present invention can be prepared as a pharmaceutical composition by admixing the active ingredient (i.e., the CRISPR-GNDM system) with known pharmaceutically acceptable carrier(s) including excipient, diluent, extender, binder, lubricant, fluidizer, disintegrant, surfactant and the like) or conventional additive(s). Examples of excipient include phosphate buffered saline (e.g., 0.01 M phosphate, 0.138 M NaCl, 0.0027 M KCl, pH 7.4), a solution containing an inorganic acid salt such as hydrochloride, hydrobromate, phosphate, sulfate or the like, saline, glycol or ethanol solution, a solution of organic acid salt such as acetate, propionate, malonate, benzoate or the like, and the like. Adjuvant(s) such as moistening agent, emulsifier and the like, and pH adjuster can also be used. Furthermore, formulation auxiliaries such as suspending agent, preservative, stabilizer, dispersant and the like may also be used. The pharmaceutical composition may be formulated in the form of dried product for re-dissolving or re-suspending with a suitable sterilized fluid immediately before use. The pharmaceutical composition can be systemically or topically administered according to dosage form, lesion area to be treated and the like. Preferably, it is topically administered. When the pharmaceutical composition is used as an injectable solution, a pharmaceutically acceptable buffer, solubilizing agent, tonicity agent or the like can be added.

The dose of the pharmaceutical of the present invention is not limited as long as it is a therapeutically effective amount. For example, when the pharmaceutical of the present invention contains the DNA encoding the CRISPR-GNDM system in the form of a viral vector, it can be administered in an amount of $10^{11}$ to $10^{13}$ vg/kg, preferably $10^{12}$ to $10^{13}$ vg/kg (as the DNA amount). The dose can vary according to kind of nucleic acid or vector, administration route, and body weight or seriousness of patient, and the like.

Since the pharmaceutical of the present invention can suppress the expression of mutant KRAS gene, it can restore the effectiveness of a known drug for a disease that has acquired resistance to said drug due to gain-of-function mutation of KRAS (e.g., G12D, G12A, G12R, G12C, G12S, G12V, G13D), including cancer such as pancreatic cancer, lung cancer and colorectal cancer). Accordingly, pharmaceutical of the present invention can be used in combination with such known drug. Examples of such drug include, but are not limited to, an antibody medicine against epidermal growth factor receptor (EGFR) (e.g., cetuximab, panitumumab) in the case of colorectal cancer having mutation in KRAS gene.

When the pharmaceutical of the present invention is used in combination with other drug, both can be mixed by a method known per se to give a fixed-dose drug, or the pharmaceutical of the present invention and other drug can be separately formulated and simultaneously or intermittently administered to the same subject. Said other drug can be administered in an amount typically used for its sole administration.

EXAMPLES

The invention will be more fully understood by reference to the following examples, which provide illustrative non-limiting embodiments of the invention.

The examples describe the use of the CRISPR-Guide Nucleotide Directed Modification (GNDM) system to suppress gene expression collectively termed "genomic modifications" herein, in the KRAS gene regulatory region that leads to the suppression of KRAS gene expression. The goal of the modifications is to reduce the impact of oncogenic KRAS products that sustain the aberrant tumor cell propagation in pancreatic cancers. Introduction of the defined therapeutic modifications represents a novel therapeutic strategy for the amelioration of tumor cell growth as described and illustrated herein.

Suppression of KRAS Gene Expression with CRISPR-GNDM System

In the following examples, we illustrate use of the methods described herein to achieve the suppression of the KRAS gene through targeting the regulatory/promoter region of the KRAS gene. The methods leverage the property of Cas9-sgRNA molecules, termed RNP, to be recruited to a desired locus of the genome by choosing an appropriate sgRNA sequence. The methods also leverage the nuclease-inactive nature of the SpCas9 protein (D10A and H840A mutant; dSpCas9) to keep the genomic sequence intact, but tether various transcriptional/epigenetic functional domains or motifs to dCas9 to achieve desired modifications of the intended loci targeted by the sgRNA sequence, as described in Gilbert et al., Cell 154, 442-451, 2013, and Gilbert et al., Cell 159, 647-661, 2014.

Figure 1:
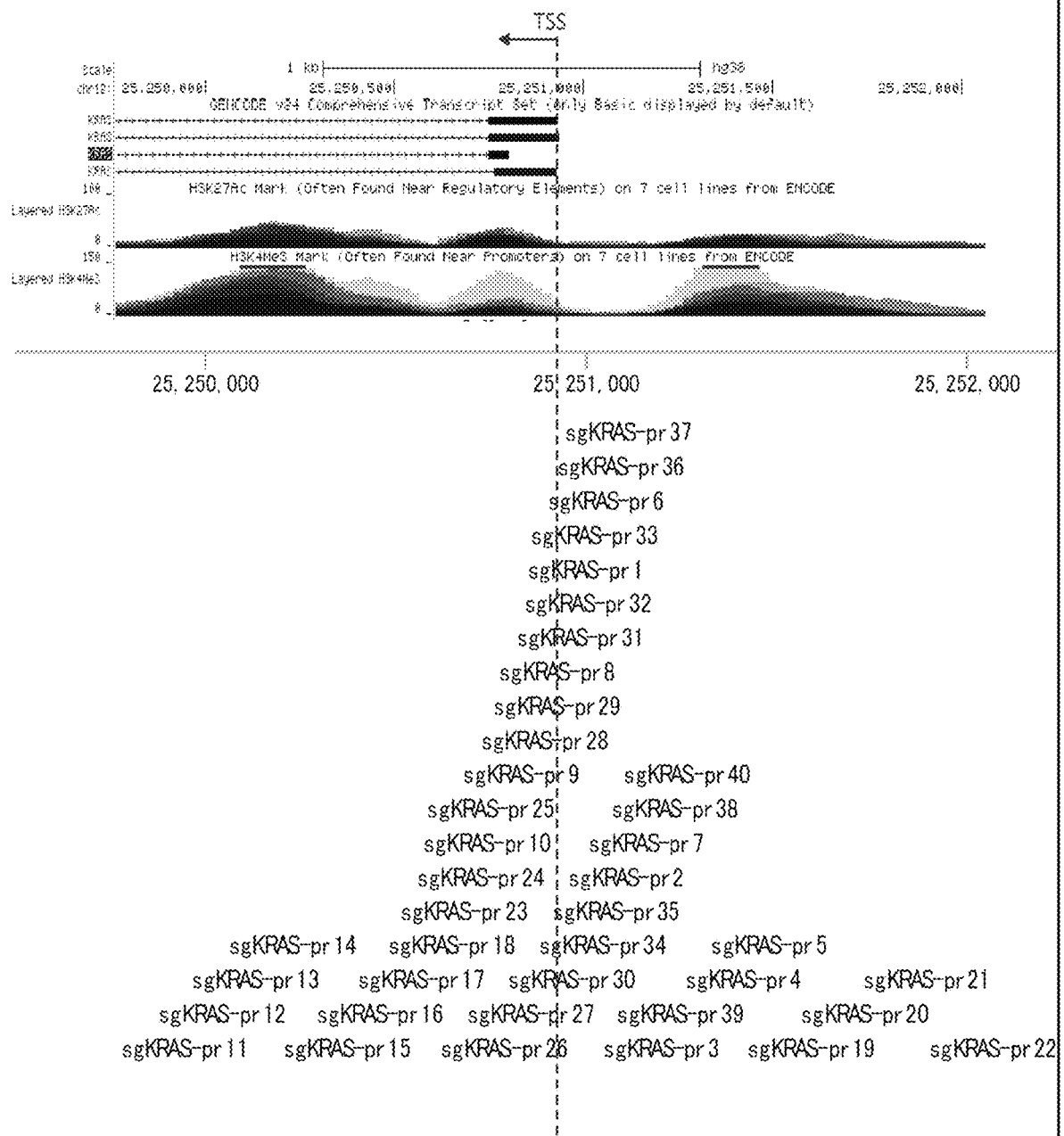
FIG. 1 shows the human KRAS locus, a predicted transcript start site (TSS), and the location of the guide RNA target sites.

In the following examples, we illustrate that the CRISPR-GNDM system can be used to suppress the expression of oncogenic KRAS gene product (e.g. G12D, G12V, G13D). Guide RNAs were designed to target the promoter region of the KRAS gene. FIG. 1 shows the human KRAS locus and a predicted transcript start site (TSS). FIG. 1 shows the promoter region of the KRAS gene, with a boxed area highlighting the critical portion of the KRAS gene promoter for its activity that involves G-quadruplex structure (Hoffman et al., PNAS 87, 2705-2709, 1990, Cogoi et at, JBC 285, 22003-22016, 2010). In FIG. 1, guide RNA sequences were designed to target the promoter-proximal region within the ~0.7 kb of the KRAS promoter, +160 to −500 base relative to the transcription start site (TSS), in order to determine the most effective therapeutic sequence within this region.

Experimental Methods

Selection of sgRNA Sequence

The promoter of the human KRAS gene contains a nuclease-hypersensitive element (NHE), which is essential for transcription (Yamamoto et al., Oncogene Res 3; 125-130, 1988, Jordano et al., Oncogene 2, 359-366, 1988, Jordano et al, Nucleic Acids Res 14, 7361-7378, 1986). Sequence around the KRAS promoter region (Chr12: 25403700-25404300) were scanned for potential sequence where dSpCas9-sgRNA RNP complex would bind. The region was scanned for protospacer adjacent motifs (PAMs) having the sequence NGG. Guide strands corresponding to the PAMs were identified. The guide sequences were selected based on predicted on-target and off-target scores generated by Benchling software (https://benchling.com), and to be evenly distributed across the selected region.

For initial screening of predicted off-target activities, there are a number of bioinformatics tools known and publicly available that can be used to predict the most likely off-target sites; and since binding to target sites in the CRISPR-Cas9 nuclease system is driven by Watson-Crick base pairing between complementary sequences, the degree of dissimilarity (and therefore reduced potential for off-target binding) is essentially related to primary sequence differences: mismatches and bulges, i.e. bases that are changed to a non-complementary base, and insertions or deletions of bases in the potential off-target site relative to the target site. An exemplary bioinformatics tool called Benchling (https://benchling.com) and COSMID (CRISPR Off-target Sites with Mismatches, Insertions and Deletions) (available on the web at https://crispr.bme.gatech.edu) compiles such similarities.

The sgRNA targeting sequences listed in Table 1 were tested for modulation function of the KRAS gene expression.

The location of the guide RNA target sites relative to the transcription start site (TSS) on the KRAS promoter (chr12: 25250929 on GRCh38/hg38 human genome assembly; NC_000012) is shown in FIG. 1.

The selected crRNA sequences were fused with the tracer RNA sequence to form single-molecule guide RNA (sgRNA) sequences, and were cloned into pCRISPR-LvSG03 sgRNA expressing vector from Genecopoeia. The sgRNA expression is driven by the U6 promoter, and the vector expresses mCherry-IRES-Puromycin gene under the SV40 promoter to facilitate tracking and selection of the sgRNA expressing cells.

Cloning of Effector Molecule

Catalytically inactive SpCas9 protein (D10A and H840A; dSpCas9) (SEQ ID NO: 59) serves as a main scaffold to tether functional domains/motifs via in a form of direct fusion proteins. dSpCas9 is attached with HA-tag peptide (SEQ ID NO: 60) in its N-terminus for tracking and detection purposes, and with two nuclear localization signal (NLS) (SEQ ID NO: 61) in its N- and C-termini to enable efficient localization of the effector molecules to the nucleus. Throughout the examples, dCas9 denotes the HA-NLS-dSpCas9 (D10A and H840A)-NLS molecule (SEQ ID NO: 62).

In one example, dCas9 protein is fused with Kruppel associated box (KRAB) motif (SEQ ID NO: 63), the 62 amino acid transcriptional repression domain, on its N- or C-termini (e.g., HA-NLS-dCas9-NLS-KRAB (SEQ ID NO: 64)). The resulting dCas9-KRAB protein is recruited to transcriptionally regulatory regions within the KRAS gene (e.g. promoter or enhance region) and thereby exerts its transcriptional repressor effect. As a consequence, the expression of KRAS gene is suppressed.

Plasmids expressing the dCas9 and dCas9-KRAB fusion protein were assembled using a vector that expressed humanized dCas9 from *S. pyogenes*. Plasmids expressing the sgRNA were assembled using complementary oligonucleotides corresponding to the guide strand (generated by Integrated DNA Technologies), phosphorylated, annealed and cloned into the sgRNA expressing vector pCRISPR-LvSG03 from Genecopoeia.

For the expression of dCas9-KRAB fusion protein, a DNA fragment encoding the dCas9-KRAB fusion protein was cloned into CP-LvC9NU-09 lentivirus expressing vector from Genecopoeia. The Cas9 coding sequence in the original vector was replaced with dCas9-KRAB coding sequence, resulting in the generation of CP-LvdCas9-KRAB-09 plasmid. The vector uses EF1a promoter for the expression of the effector molecules, and SV40 promoter to express eGFP-IRES-Neomycin gene.

Cell Culture and Transfection

HEK293FT cells were seeded 24 hours prior to transfection in 24-well plates at a density of 75,000 cells per well and cultured in DMEM media supplemented with 10% FBS and 2 mM fresh L-glutamine, 1 mM sodium pyruvate and non-essential amino acids. HEK293FT cells were co-transfected with 250 ng of CP-LvdCas9-09 plasmid or CP-LvdCas9-KRAB-09 plasmid and 250 ng of the pCRISPR-LvSG03 sgRNA expressing plasmids (No. 1-40) in 24-well plate. The transfected cells were harvested on day 4 and the total RNA was isolated using Qiagen Rneasy kit. The expression level of the KRAS gene was normalized by the expression of HPRT gene in each sample. The effect of suppression by dCas9-KRAB was shown for each sgRNA relative to no effector (sgRNA only) samples. Experiments were repeated three times and the average and SD were shown.

PANC1 cells were cultured in DMEM media supplemented with 10% (vol/vol) heat-inactivated 10% FBS and 2 mM fresh L-glutamine 100 units/mL penicillin, and 100 µg/mL streptomycin. The cell cultures were maintained in a humidified atmosphere of 5% (vol/vol) $CO_2$ at 37° C. The cells were passaged as they approached a confluency of $1 \times 10^5$/ml. Lipofectamine 2000 was used to transfect 100,000 cells with 500 ng of vector expressing KRAS targeting sgRNAs, and plasmid expressing dCas9-effector molecules following manufacturer's instructions.

MiaPaca-2 (CRM) cells were cultured in DMEM media supplemented with 10% 10% (vol/vol) heat-inactivated FBS and 2 mM fresh L-glutamine 100 units/mL penicillin, and 100 µg/mL streptomycin. The cell cultures were maintained in a humidified atmosphere of 5% (vol/vol) $CO_2$ at 37° C. The cells were passaged as they approached a confluency of $1 \times 10^5$/ml. Lipofectamine 2000 was used to transfect 75,000 cells with 500 ng of vector expressing KRAS targeting sgRNAs and plasmid expressing dCas9-effector molecules following manufacturer's instructions.

For gene expression analysis, the transfected cells were harvested at 48-72 h after transfection and lysed in RLT buffer (Qiagen) to extract total RNA using RNeasy kit (Qiagen). For protein analysis, the transfected cells were harvested at 96 h post-transfection in lysis buffer for RNA isolation and protein analysis as described below.

Plasmids for Lentivirus Production

The selected guide RNA sequences below were fused with the tracer RNA sequence to form single-molecule guide RNA (sgRNA) sequences, and were cloned into pLentiCRISPRv2-EFS-dspC9-KRAB-P2A-Puro expressing vector from Genescript. The sgRNA expression is driven by the hU6 promoter, and the vector expresses the puromycin gene under the EFS promoter to facilitate tracking and selection of the sgRNA expressing cells.

per Taqman reaction. The Taqman primers and probes for the KRAS gene was obtained from Applied Biosystems. Taqman reaction was run using Taqman gene expression master mix (ThermoFisher) in Roche LightCycler 96 or LightCycler 480 and analyzed using LightCycler 96 analysis software.

TABLE 4

| Guide RNA No (SEQ ID NO) | Position | Strand | Sequence | PAM | Specificity Score | Efficiency Score |
|---|---|---|---|---|---|---|
| 1 | 25403769 | 1 | TCGCTCCCAGTCCGAAATGG | CGG | 89.4 | 57.4 |
| 6 | 25403808 | -1 | GGCAGTGGCGGCGGCGAAGG | TGG | 48.6 | 45.8 |
| 8 | 25403680 | -1 | TGCGGGAGAGAGGTACGGAG | CGG | 41.9 | 68.4 |
| 10 | 25403482 | -1 | CGCGGGGAGTGAGGAATGGG | CGG | 28.9 | 63.1 |
| 34 | 25250850 | -1 | GGCGGCTCGGCCAGTACTCC | CGG | 76.3 | 37.9 |
| 35 | 25250886 | -1 | AGCAGCGGCGGCGGCAGTGG | CGG | 32.5 | 41.0 |

Lentivirus Production and Transduction

Lentiviral particles were generated using HEK293Ta cells seeded at a density of 500,000 cells per well in 6-well plates and cultured in DMEM media supplemented with 10% FBS and 2 mM fresh L-glutamine, 1 mM sodium pyruvate and non-essential amino acids. Cells were transfected with 2 μg of lenti-pac HIV plasmid mix (Genecopoeia) and 2 μg of pLentiCRISPRv2-EFS-dspC9-KRAB-P2A-Puro with SpCas9 sgRNA AIO (all-in-one) plasmid with 5 μl Endofectin (Genecopoeia) according to manufacturer's instructions. After 16 h incubation, media was aspirated and replaced with 2 ml of fresh DMEM. After 48 h, media was collected and filter sterilized (0.45 μm, VWR) before transduction.

In order to transduce MiaPaca2 and PANC1 cells, 100,000 cells per well were seeded in 24-well plates and incubated for 16 h in appropriate medium as described. Media was replaced with 700 μl fresh media, 300 μl filter sterilized lentivirus, and 5 μg/ml polybrene (Sigma) to a final concentration of 5 μg/ml. After a subsequent 16 h incubation, cells were trypsinized with 0.25% trypsin-EDTA and seeded into 6-well plates, followed by a 16 h incubation. Successfully transduced MiaPaca2 and PANC1 cells were selected by addition of media with 2 μg/ml puromycin (Sigma). Knockdown efficiency of KRAS was determined as described in 'gene expression analysis' by Taqman.

Cell Proliferation Assay

Stably selected with 2 μg/ml puromycin (Sigma) MiaPaca2 and PANC1 cells were trypsinized with 0.25% trypsin-EDTA and seeded into 96-well plates at 5000 cells per well and incubated for 16 h in appropriate medium as described. Media was aspirated, cells washed with 1×PBS followed by aspiration and replacement with serum-free fresh media. After 24/48/72/96 h, Cell Counting Kit-8 (Dojindo) substrate was added and cell numbers determined according to manufacturer's instructions.

Gene Expression Analysis

For Taqman analysis, 1.5 μg of total RNA was used to generate cDNA using TaqMan™ High-Capacity RNA-to-cDNA Kit (Applied Biosystems) in 20 μl volume. The generated cDNA was diluted 20 fold and 6.33 μl was used Taqman Probe Product IDs:
Kras: Hs00364284g_1 (FAM)
HPRT: Hs99999909_m1 (FAM, VIC)
Taqman QPCR condition:
Step 1; 95° C. 10 min
Step 2; 95° C. 15 sec
Step 3; 60° C. 30 sec
Repeat Step 2 and 3; 40 times
Xenograft Models and Tumor Volume Measurements:

6 to 10 week-old immunocompromised NOD.Cg-Prkdscid Il2rgtmWjl/SzJ (NSG mice—Jackson Laboratory) and CrTac:NCr-Foxn1-nu (Nude mice—Taconic) were used as xenograft models for pancreatic cancer cell lines PANC1 and Miapaca2. Cells transduced with CRISPR-GNDM system and the most efficient sgRNA (sgRNA #6) were generated and positively selected as discussed in the previous section. Transduced and wild type control cells were fed with fresh media one day before the injections. On the day of experiment, cells were trypsinized, centrifuged and resuspended in 200 μl of 1:1 matrigel (Corning) and serum-free media mixture. Mice were anesthetized with isoflurane and 10 million cells were injected subcutaneously into the right flanks by using an insulin syringe with a 25 G needle. Tumor sizes were measured on day 9 following the injections and then weekly by an electronic caliper. Tumor volumes were calculated by using the following formula: $(length) \times (width^2)/2$.

Results

FIG. 1 shows the position of sgRNA used in this example.

Figure 2:
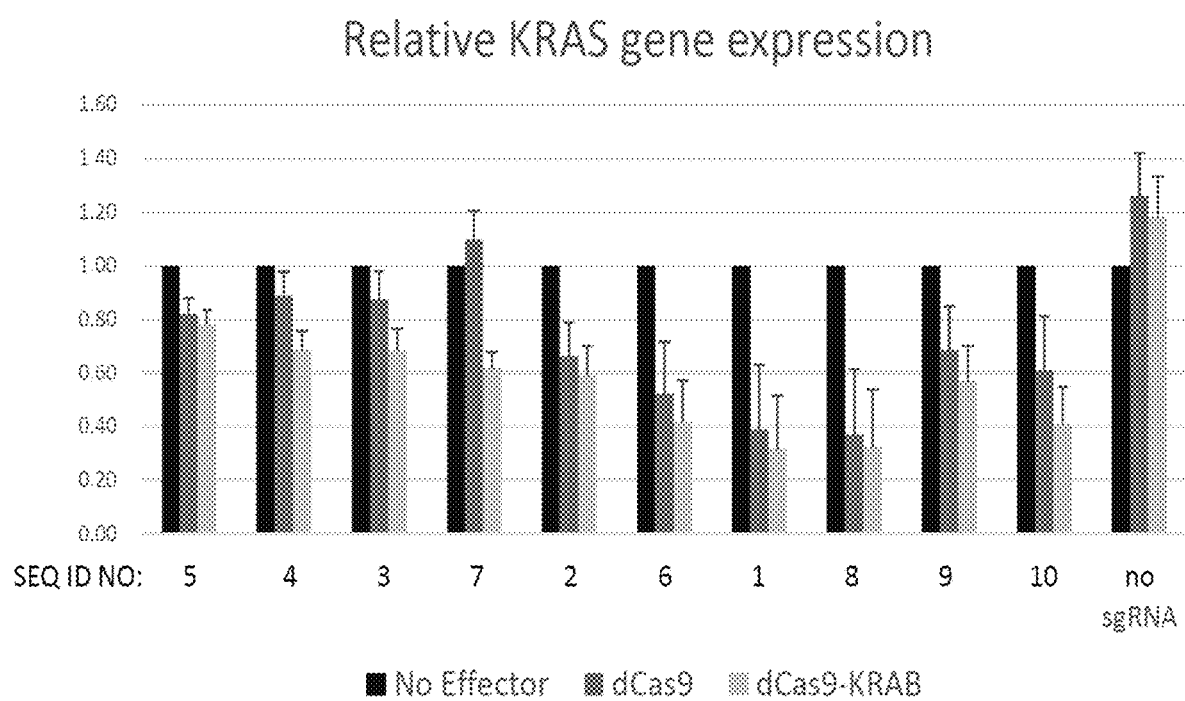
FIG. 2 shows KRAS gene suppression by dCas9 protein alone or dCas9-KRAB fusion protein. HEK293FT cells were co-transfected with 250 ng of CP-LvdCas9-09 plasmid or CP-LvdCas9-KRAB-09 plasmid and 250 ng of the pCRISPR-LvSG03 gN expressing plasmids (SEQ ID NOs.

FIG. 2 shows suppression of KRAS gene expression by dCas9 protein alone or dCas9-KRAB fusion protein. The sgRNAs of SEQ ID Nos: 1-10 suppressed KRAS gene expression by recruiting dCas9 to a regulatory region of KRAS gene. The suppression effect was enhanced by combining KRAB fusion.

FIG. 3 shows suppression of KRAS gene expression by dCas9-KRAB fusion protein. The sgRNAs of SEQ ID Nos: 1-22 suppressed KRAS gene expression by recruiting dCas9 to a regulatory region of KRAS gene. The effective suppression was observed by the sgRNAs indicated as "Effective region".

FIG. 4 shows suppression of KRAS gene expression by dCas9-KRAB fusion protein and sgRNAs designed within the "effective region" identified in FIG. 3 (SEQ ID Nos: 23-40). The effective suppression was observed with the sgRNAs indicated by the arrows (SEQ ID Nos: 1, 6, 8, 10, 23, 24, 31, 32, 34, 35).

FIGS. 5 and 6 show suppression of cell growth in vitro of PANC1 and MiaPaca2 cells stably expressing dCas9-KRAB fusion protein and sgRNAs indicated (SEQ ID Nos: 1, 6, 8, 10, 34, 35). The bottom bar graphs show the suppression of KRAS gene in the stable cell lines. The most effective suppression of growth was observed sgRNA #6 (SEQ ID No: 6) and #35 (SEQ ID NO: 35).

FIGS. 7 and 8 show suppression of tumor growth in vivo of PANC1 and MiaPaca2 cells stable expressing dCas9-KRAB fusion protein and sgRNA #6. Nude mice and NSG mice were transplanted with the stably expressing cells and the tumor size was measured from week 1 to 4. In both experiments, cells expressing dCas9-KRAB and sgRNA #6 showed slower tumor growth than the parent cells.

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

In addition, the contents disclosed in any publication cited herein, including patents and patent applications, are hereby incorporated in their entireties by reference, to the extent that they have been disclosed herein.

This application is based on U.S. provisional patent application Ser. No. 62/455,845 (filing date: Feb. 7, 2017) and U.S. provisional patent application Ser. No. 62/626,232 (filing date: Feb. 5, 2018), the contents of which are incorporated in full herein by this reference.

INDUSTRIAL APPLICABILITY

As described in detail above, the CRISPR-GNDM system of the present invention may be used for the treatment of a disease associated with elevated KRAS activity or expression in a subject.

The invention claimed is:

1. A CRISPR-Guide Nucleotide Directed Modulation (GNDM) system for suppressing KRAS expression comprising (a) a protein selected from the group consisting of dCas9 car dCpf1, a fusion protein of dCas9 or dCpf1 and Kruppel associated box (KRAB), and (b) a guide nucleotide (gN) targeting an expression regulatory region of KRAS gene,
wherein the gN comprises a sequence complementary to the expression regulatory region of KRAS gene and consisting of 18-25 nucleotides, and
the gN comprises a nucleotide sequence represented by SEQ ID NO: 1, 6, 8, 10, 23, 24, 31, 32, 34 or 35, or a part of the sequence.

2. The CRISPR-GNDM system of claim 1, wherein the expression regulatory region of KRAS gene is a region having the nucleotide sequence shown by SEQ ID NO: 65.

3. The CRISPR-GNDM system of claim 1, wherein the expression regulatory region of KRAS gene is a region having the nucleotide sequence at positions 81-545, preferably 134-532, of SEQ ID NO: 65.

4. The CRISPR-GNDM system of claim 1, wherein the gN comprises a nucleotide sequence represented by SEQ ID NO: 6, 8, 34 or 35.

5. The CRISPR-GNDM system of claim 1, wherein the gN comprises a sequence complementary to the expression regulatory region of KRAS gene and consisting of 20-24 nucleotides.

6. The CRISPR-GNDM system of claim 1, wherein the sequence complementary to the expression regulatory region of KRAS gene consists of 20 nucleotides.

7. The CRISPR-GNDM system of claim 1, wherein the gN comprises a nucleotide sequence represented by SEQ ID NO: 6 or 35.

8. The CRISPR-GNDM system of claim 1, wherein the gN comprises a nucleotide sequence represented by SEQ ID NO: 6.

* * * * *

SEQUENCE LISTING

```
<160> NUMBER OF SEQ ID NOS: 65

<210> SEQ ID NO 1
<211> LENGTH: 20
<212> TYPE: RNA
<213> ORGANISM: Homo sapiens

<400> SEQUENCE: 1
ucgcucccag uccgaaaugg                                                 20

<210> SEQ ID NO 2
<211> LENGTH: 20
<212> TYPE: RNA
<213> ORGANISM: Homo sapiens

<400> SEQUENCE: 2
cggagcucga uuuuccuagg                                                 20

<210> SEQ ID NO 3
<211> LENGTH: 20
<212> TYPE: RNA
<213> ORGANISM: Homo sapiens

<400> SEQUENCE: 3
cuucagacgg gcguacgaga                                                 20

<210> SEQ ID NO 4
<211> LENGTH: 20
<212> TYPE: RNA
<213> ORGANISM: Homo sapiens

<400> SEQUENCE: 4
gagggacugc cggacccacg                                                 20

<210> SEQ ID NO 5
<211> LENGTH: 20
<212> TYPE: RNA
<213> ORGANISM: Homo sapiens

<400> SEQUENCE: 5
gucccgcucc gggucagaau                                                 20
```

```
<210> SEQ ID NO 6
<211> LENGTH: 20
<212> TYPE: RNA
<213> ORGANISM: Homo sapiens

<400> SEQUENCE: 6
ggcaguggcg gcggcgaagg                                               20

<210> SEQ ID NO 7
<211> LENGTH: 20
<212> TYPE: RNA
<213> ORGANISM: Homo sapiens

<400> SEQUENCE: 7
aucgauagcu cugcccucug                                               20

<210> SEQ ID NO 8
<211> LENGTH: 20
<212> TYPE: RNA
<213> ORGANISM: Homo sapiens

<400> SEQUENCE: 8
ugcgggagag agguacggag                                               20

<210> SEQ ID NO 9
<211> LENGTH: 20
<212> TYPE: RNA
<213> ORGANISM: Homo sapiens

<400> SEQUENCE: 9
aaugaauuag ggguccccgg                                               20

<210> SEQ ID NO 10
<211> LENGTH: 20
<212> TYPE: RNA
<213> ORGANISM: Homo sapiens

<400> SEQUENCE: 10
cgcggggagu gaggaauggg                                               20

<210> SEQ ID NO 11
<211> LENGTH: 20
<212> TYPE: RNA
<213> ORGANISM: Homo sapiens

<400> SEQUENCE: 11
gguaguauaa aagagacgag                                               20

<210> SEQ ID NO 12
<211> LENGTH: 20
<212> TYPE: RNA
<213> ORGANISM: Homo sapiens

<400> SEQUENCE: 12
cugucuacac ucaacuagca                                               20

<210> SEQ ID NO 13
<211> LENGTH: 20
<212> TYPE: RNA
<213> ORGANISM: Homo sapiens

<400> SEQUENCE: 13
aggaaaaagu uaaucccaga                                               20
```

<210> SEQ ID NO 14
<211> LENGTH: 20
<212> TYPE: RNA
<213> ORGANISM: Homo sapiens

<400> SEQUENCE: 14
ugacauugcu guggccacaa                                                  20

<210> SEQ ID NO 15
<211> LENGTH: 20
<212> TYPE: RNA
<213> ORGANISM: Homo sapiens

<400> SEQUENCE: 15
ggauguguga guaagagggg                                                  20

<210> SEQ ID NO 16
<211> LENGTH: 20
<212> TYPE: RNA
<213> ORGANISM: Homo sapiens

<400> SEQUENCE: 16
uagagaugcc aaaugcagca                                                  20

<210> SEQ ID NO 17
<211> LENGTH: 20
<212> TYPE: RNA
<213> ORGANISM: Homo sapiens

<400> SEQUENCE: 17
ugcgguggag guuacucccg                                                  20

<210> SEQ ID NO 18
<211> LENGTH: 20
<212> TYPE: RNA
<213> ORGANISM: Homo sapiens

<400> SEQUENCE: 18
uuccuccucc ccgagagccg                                                  20

<210> SEQ ID NO 19
<211> LENGTH: 20
<212> TYPE: RNA
<213> ORGANISM: Homo sapiens

<400> SEQUENCE: 19
ugcucuucgc agcuucucug                                                  20

<210> SEQ ID NO 20
<211> LENGTH: 20
<212> TYPE: RNA
<213> ORGANISM: Homo sapiens

<400> SEQUENCE: 20
gcggacgauu ucccacaccg                                                  20

<210> SEQ ID NO 21
<211> LENGTH: 20
<212> TYPE: RNA
<213> ORGANISM: Homo sapiens

<400> SEQUENCE: 21

```
gauauuuuga acccaucaca                                                      20

<210> SEQ ID NO 22
<211> LENGTH: 20
<212> TYPE: RNA
<213> ORGANISM: Homo sapiens

<400> SEQUENCE: 22
aguuaagaca uuaaacaaug                                                      20

<210> SEQ ID NO 23
<211> LENGTH: 20
<212> TYPE: RNA
<213> ORGANISM: Homo sapiens

<400> SEQUENCE: 23
cguccaggaa gcagcaccag                                                      20

<210> SEQ ID NO 24
<211> LENGTH: 20
<212> TYPE: RNA
<213> ORGANISM: Homo sapiens

<400> SEQUENCE: 24
gggcggugcg gggcugagga                                                      20

<210> SEQ ID NO 25
<211> LENGTH: 20
<212> TYPE: RNA
<213> ORGANISM: Homo sapiens

<400> SEQUENCE: 25
acgcggcggc gcggggagug                                                      20

<210> SEQ ID NO 26
<211> LENGTH: 20
<212> TYPE: RNA
<213> ORGANISM: Homo sapiens

<400> SEQUENCE: 26
cugggugaga ggggucugca                                                      20

<210> SEQ ID NO 27
<211> LENGTH: 20
<212> TYPE: RNA
<213> ORGANISM: Homo sapiens

<400> SEQUENCE: 27
gcggcgagug aaugaauuag                                                      20

<210> SEQ ID NO 28
<211> LENGTH: 20
<212> TYPE: RNA
<213> ORGANISM: Homo sapiens

<400> SEQUENCE: 28
ggcaaagagg gucgggaccc                                                      20

<210> SEQ ID NO 29
<211> LENGTH: 20
<212> TYPE: RNA
<213> ORGANISM: Homo sapiens

<400> SEQUENCE: 29
```

```
cggagcggac cacccucccu                                              20

<210> SEQ ID NO 30
<211> LENGTH: 20
<212> TYPE: RNA
<213> ORGANISM: Homo sapiens

<400> SEQUENCE: 30
ccagaggcuc agcggcuccc                                              20

<210> SEQ ID NO 31
<211> LENGTH: 20
<212> TYPE: RNA
<213> ORGANISM: Homo sapiens

<400> SEQUENCE: 31
aggcacugaa ggcggcggcg                                              20

<210> SEQ ID NO 32
<211> LENGTH: 20
<212> TYPE: RNA
<213> ORGANISM: Homo sapiens

<400> SEQUENCE: 32
acugggagcg agcgcggcgc                                              20

<210> SEQ ID NO 33
<211> LENGTH: 20
<212> TYPE: RNA
<213> ORGANISM: Homo sapiens

<400> SEQUENCE: 33
aguccgaaau ggcggggggcc                                             20

<210> SEQ ID NO 34
<211> LENGTH: 20
<212> TYPE: RNA
<213> ORGANISM: Homo sapiens

<400> SEQUENCE: 34
ggcggcucgg ccaguacucc                                              20

<210> SEQ ID NO 35
<211> LENGTH: 20
<212> TYPE: RNA
<213> ORGANISM: Homo sapiens

<400> SEQUENCE: 35
agcagcggcg gcggcagugg                                              20

<210> SEQ ID NO 36
<211> LENGTH: 20
<212> TYPE: RNA
<213> ORGANISM: Homo sapiens

<400> SEQUENCE: 36
cgcugcugcc uccgccgccg                                              20

<210> SEQ ID NO 37
<211> LENGTH: 20
<212> TYPE: RNA
<213> ORGANISM: Homo sapiens
```

```
<400> SEQUENCE: 37
auuuuccuag gcggcggccg                                              20

<210> SEQ ID NO 38
<211> LENGTH: 20
<212> TYPE: RNA
<213> ORGANISM: Homo sapiens

<400> SEQUENCE: 38
ggagcggcug agggcggugu                                              20

<210> SEQ ID NO 39
<211> LENGTH: 20
<212> TYPE: RNA
<213> ORGANISM: Homo sapiens

<400> SEQUENCE: 39
cgguguggga agagggaaga                                              20

<210> SEQ ID NO 40
<211> LENGTH: 20
<212> TYPE: RNA
<213> ORGANISM: Homo sapiens

<400> SEQUENCE: 40 gaggggagg cagcgagcgc                                               20

<210> SEQ ID NO 41
<211> LENGTH: 22
<212> TYPE: RNA
<213> ORGANISM: Homo sapiens

<400> SEQUENCE: 41
ccaguccgaa auggcggggg cc                                           22

<210> SEQ ID NO 42
<211> LENGTH: 22
<212> TYPE: RNA
<213> ORGANISM: Homo sapiens

<400> SEQUENCE: 42
aaaucgagcu ccgagcacac cg                                           22

<210> SEQ ID NO 43
<211> LENGTH: 22
<212> TYPE: RNA
<213> ORGANISM: Homo sapiens

<400> SEQUENCE: 43
ccucucguac gcccgucuga ag                                           22

<210> SEQ ID NO 44
<211> LENGTH: 22
<212> TYPE: RNA
<213> ORGANISM: Homo sapiens

<400> SEQUENCE: 44
cgggggccgg gccggcggag ga                                           22

<210> SEQ ID NO 45
<211> LENGTH: 22
<212> TYPE: RNA
<213> ORGANISM: Homo sapiens
```

```
<400> SEQUENCE: 45 ggaagggug gcuggggcgg uc                                              22

<210> SEQ ID NO 46
<211> LENGTH: 22
<212> TYPE: RNA
<213> ORGANISM: Homo sapiens

<400> SEQUENCE: 46
ggcgagccgg gccggcugga ga                                             22

<210> SEQ ID NO 47
<211> LENGTH: 22
<212> TYPE: RNA
<213> ORGANISM: Homo sapiens

<400> SEQUENCE: 47
uaggcagggg gcgggccgcc gc                                             22

<210> SEQ ID NO 48
<211> LENGTH: 22
<212> TYPE: RNA
<213> ORGANISM: Homo sapiens

<400> SEQUENCE: 48
gcgguccggu cccgcuccgg gu                                             22

<210> SEQ ID NO 49
<211> LENGTH: 22
<212> TYPE: RNA
<213> ORGANISM: Homo sapiens

<400> SEQUENCE: 49
cccgccgcgg uccggucccg cu                                             22

<210> SEQ ID NO 50
<211> LENGTH: 22
<212> TYPE: RNA
<213> ORGANISM: Homo sapiens

<400> SEQUENCE: 50
ggaccggacc gcggcgggcu gu                                             22

<210> SEQ ID NO 51
<211> LENGTH: 23
<212> TYPE: RNA
<213> ORGANISM: Homo sapiens

<400> SEQUENCE: 51
ggacugggag cgagcgcggc gca                                            23

<210> SEQ ID NO 52
<211> LENGTH: 23
<212> TYPE: RNA
<213> ORGANISM: Homo sapiens

<400> SEQUENCE: 52
cuaggcggcg gccgcggcgg cgg                                            23

<210> SEQ ID NO 53
<211> LENGTH: 23
<212> TYPE: RNA
```

<213> ORGANISM: Homo Sapiens

<400> SEQUENCE: 53
ccuaggcggc ggccgcggcg gcg                                                    23

<210> SEQ ID NO 54
<211> LENGTH: 12
<212> TYPE: RNA
<213> ORGANISM: Streptococcus pyogenes
<220> FEATURE:
<221> NAME/KEY: misc_structure
<222> LOCATION: (1)..(12)
<223> OTHER INFORMATION: crRNA direct repeat sequence

<400> SEQUENCE: 54
guuuuagagc ua                                                                12

<210> SEQ ID NO 55
<211> LENGTH: 14
<212> TYPE: RNA
<213> ORGANISM: Streptococcus pyogenes
<220> FEATURE:
<221> NAME/KEY: misc_structure
<222> LOCATION: (1)..(14)
<223> OTHER INFORMATION: tracrRNA anti-repeat region

<400> SEQUENCE: 55
uagcaaguua aaau                                                              14

<210> SEQ ID NO 56
<211> LENGTH: 48
<212> TYPE: RNA
<213> ORGANISM: Streptococcus pyogenes
<220> FEATURE:
<221> NAME/KEY: misc_structure
<222> LOCATION: (1)..(48)
<223> OTHER INFORMATION: tracrRNA subsequent stem-loop 1, linker,
      stem-loop 2 and stem-loop 3 regions

<400> SEQUENCE: 56
aaggcuaguc cguuaucaac uugaaaaagu ggcaccgagu cggugcuu                          48

<210> SEQ ID NO 57
<211> LENGTH: 19
<212> TYPE: RNA
<213> ORGANISM: Francisella novicida
<220> FEATURE:
<221> NAME/KEY: misc_structure
<222> LOCATION: (1)..(19)
<223> OTHER INFORMATION: crRNA direct repeat sequence

<400> SEQUENCE: 57
aauuucuacu cuuguagau                                                         19

<210> SEQ ID NO 58
<211> LENGTH: 3001
<212> TYPE: DNA
<213> ORGANISM: Homo sapiens

<400> SEQUENCE: 58
aaatagacct ttcccattta taacttattt gtaaaatgat ttctattata aacataacat            60
atacattgta taacaattag aaaacctgtc tgttttgatg gatctcaaga tttaagaagg           120
cttagacttc agctataaga tgcacatgcc actgtgggag gccgaggcgg gcagatcacg           180
aggtcaggag ttctagacca gcctgaccaa catggtgaaa cccccgtctc tactaaaaat           240

| | |
|---|---|
| acaaaaaatt agccgggcat ggcagcagac acctgtaatc ccagttattc gggaggctga | 300 |
| ggcaggagaa ttgcttgaat gcaggaggca gaggttgcag tgagccgaga cggcgccact | 360 |
| gcactccagc ctgggcaaca gagcagatgg agaccatcct gaccaacatg atgaaactct | 420 |
| gtctctacta aaaatacaaa aattagctgg gcatggtggc gtgcacctac tagtcccagc | 480 |
| tactcgggag gctgaggcag gagaattgct tgaacccagg aggcggaggt ttcagtgagc | 540 |
| cgataccgcg ccattgcact ccagcctggg caacagagcg agactgtgtc tcaaaaaaaa | 600 |
| aaaaaaaaag gagatgcaca tgtttaagtc tatttcaggc ggttagctgg tggattgcta | 660 |
| caattcctct gtaagtttaa aaaatcatgt aagtgctgtt ttggagtact gtaataactc | 720 |
| ttgagatgta gaacacatct gcaaaatgag ggtagtataa aagagacgag gggatgaggg | 780 |
| taatacataa gaaatagggg aaaggacaag aacaggtaaa ttaaacttca agtactattt | 840 |
| ttgctattgc tgtctacact caactagcaa ggaaaaagcc ttgcttctgc tctgcgggtt | 900 |
| ttcttcgggt ttaacttgac caagcaaaac agaccatctg ggattaactt tttccttttc | 960 |
| actgtaggtc acaggctcta cgtgtagggt gttggccacc tgttcttcca ccatctctac | 1020 |
| ctccacctcc tcctttgtgg ccacagcaat gtcacagccc atacatgggg gaggggagca | 1080 |
| ttcaggaact cggaggcaga tgcatttttt tccaaacaca ataacctcaa acagtggtct | 1140 |
| ctaagcactt tcctatgctc ttccaaaacg tgacctcccc tcttactcac atatcccccta | 1200 |
| cacacgaaaa aggaccacta tccgtccagc ctgcgctcga gggagaagtt tataccttcg | 1260 |
| tcctagagat gccaaatgca gcagggaagg ctggaccgag gcagccgagt gctggaaagg | 1320 |
| gaggcaagag gtgcgggagc ggggagaggg ggaggggagg ccggggcgcc gcgggagtaa | 1380 |
| cctccaccgc accccaccgc tccgaggggc agccggcccg gcccgagttt ctccccagaa | 1440 |
| gcctccagcc gcggctctcg gggaggagga aggaagggt tccccgtcca ggaagcagca | 1500 |
| ccagcggcga ccgcctccag cctcaccctc ctcagcccg caccgcccat tcctcactcc | 1560 |
| ccgcgccgcc gcgtccgcgc gcctcccccc tgcagacccc tctcacccag cccgcccga | 1620 |
| cccccgcgccc gcgccccca cccgcccctc cggggacccc taattcattc actcgccgcc | 1680 |
| ggccccgccc ggcgccggca aagagggtcg ggacccgggc aggggcccag gaggggtggt | 1740 |
| ccgctccgta cctctctccc gcacctggga gccgctgagc ctctggcccc gccgccgcct | 1800 |
| tcagtgcctg cgccgcgctc gctcccagtc cgaaatggcg ggggccggga gtactggccg | 1860 |
| agccgccgcc accttcgccg ccgccactgc cgccgccgct gctgcctccg ccgccgcggc | 1920 |
| cgccgcctag gaaaatcgag ctccgagcac accgatgagt tcggggccgg gcggccgcag | 1980 |
| agggcagagc tatcgatgcg ttccgcgctc gattcttctt cagacgggcg tacgagaggg | 2040 |
| agcggctgag ggcggtgtgg gaagagggaa gaggggagg cagcgagcgc cggcggggag | 2100 |
| aaggaggggg ccgggccggg ccggcggggg aggagcgggg gccgggccgg cggaggaagg | 2160 |
| ggtggctggg gcggtctagg gtggcgagcc gggccggctg gagagcgggt ctgggcggcg | 2220 |
| ccttggcggg aggagggact gccggaccca cgcggcggcc cgcccctgc ctagccgcaa | 2280 |
| ggctgtcccc gcagccgcca attctgaccc ggagcgggac cggaccgcgg cgggctgtgc | 2340 |
| ggatgccacc agggagacgc cgcgagcggc cacgccgccc cgctgaccgg tctccacaga | 2400 |
| gaagctgcga agagcacccc gccaccctca gggtcggcct atactggcgc gcatccattt | 2460 |
| actatcattg actgcatgta aataaacaag cagtcaccaa aagtgggagg cgacttcggg | 2520 |
| gacttaggga gaccgggcgg acgatttccc acaccggggc tgtctgatcg ccgccccgat | 2580 |
| tattatcagc ctcagcactt gggctgggaa tttagcccca ggcccaaaca aacacgacag | 2640 |

```
acccttttcaa cgctaatctt ctcgggtcag gaggcttgtg atattttgct atctttcttg   2700
atattttgaa cccatcacaa ggtctctaaa cagggacttc gcttataccc agggcccctg   2760
aaatcacaaa caaagacaa ctgttttta gtagagatgg ccttggtagt ttagacctga     2820
ggagagtcat tcaaacatta attagaagac agattaatca gttaaagttc gtggagttaa   2880
gacattaaac aatggggcaa ttaaacatgc tagcataccc ggagtctgtg ttgataaact   2940
acctagaaat gtatcttggg agagtcttga ggattgaggg ctggaaaagc agcgcctgta   3000
c                                                                   3001
```

<210> SEQ ID NO 59
<211> LENGTH: 1367
<212> TYPE: PRT
<213> ORGANISM: Streptococcus pyogenes

<400> SEQUENCE: 59

```
Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300
```

-continued

```
Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
            325                 330                 335

Leu Val Arg Gln Gln Leu Pro Glu Lys Tyr Lys Glu Ile Phe Phe Asp
        340                 345                 350

Gln Ser Lys Asn Gly Tyr Ala Gly Tyr Ile Asp Gly Gly Ala Ser Gln
    355                 360                 365

Glu Glu Phe Tyr Lys Phe Ile Lys Pro Ile Leu Glu Lys Met Asp Gly
370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
            405                 410                 415

Glu Leu His Ala Ile Leu Arg Arg Gln Glu Asp Phe Tyr Pro Phe Leu
        420                 425                 430

Lys Asp Asn Arg Glu Lys Ile Glu Lys Ile Leu Thr Phe Arg Ile Pro
    435                 440                 445

Tyr Tyr Val Gly Pro Leu Ala Arg Gly Asn Ser Arg Phe Ala Trp Met
450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
            485                 490                 495

Phe Asp Lys Asn Leu Pro Asn Glu Lys Val Leu Pro Lys His Ser Leu
        500                 505                 510

Leu Tyr Glu Tyr Phe Thr Val Tyr Asn Glu Leu Thr Lys Val Lys Tyr
    515                 520                 525

Val Thr Glu Gly Met Arg Lys Pro Ala Phe Leu Ser Gly Glu Gln Lys
530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
            565                 570                 575

Val Glu Ile Ser Gly Val Glu Asp Arg Phe Asn Ala Ser Leu Gly Thr
        580                 585                 590

Tyr His Asp Leu Leu Lys Ile Ile Lys Asp Lys Asp Phe Leu Asp Asn
    595                 600                 605

Glu Glu Asn Glu Asp Ile Leu Glu Asp Ile Val Leu Thr Leu Thr Leu
610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
            645                 650                 655

Gly Trp Gly Arg Leu Ser Arg Lys Leu Ile Asn Gly Ile Arg Asp Lys
        660                 665                 670

Gln Ser Gly Lys Thr Ile Leu Asp Phe Leu Lys Ser Asp Gly Phe Ala
    675                 680                 685

Asn Arg Asn Phe Met Gln Leu Ile His Asp Asp Ser Leu Thr Phe Lys
690                 695                 700

Glu Asp Ile Gln Lys Ala Gln Val Ser Gly Gln Gly Asp Ser Leu His
705                 710                 715                 720
```

```
Glu His Ile Ala Asn Leu Ala Gly Ser Pro Ala Ile Lys Lys Gly Ile
            725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
            755                 760                 765

Thr Gln Lys Gly Gln Lys Asn Ser Arg Glu Arg Met Lys Arg Ile Glu
            770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
            805                 810                 815

Asn Gly Arg Asp Met Tyr Val Asp Gln Glu Leu Asp Ile Asn Arg Leu
            820                 825                 830

Ser Asp Tyr Asp Val Asp Ala Ile Val Pro Gln Ser Phe Leu Lys Asp
            835                 840                 845

Asp Ser Ile Asp Asn Lys Val Leu Thr Arg Ser Asp Lys Asn Arg Gly
            850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
            885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
            915                 920                 925

His Val Ala Gln Ile Leu Asp Ser Arg Met Asn Thr Lys Tyr Asp Glu
            930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr Pro Lys Leu Glu Ser Glu Phe Val
            995                 1000                1005

Tyr Gly Asp Tyr Lys Val Tyr Asp Val Arg Lys Met Ile Ala Lys
            1010                1015                1020

Ser Glu Gln Glu Ile Gly Lys Ala Thr Ala Lys Tyr Phe Phe Tyr
            1025                1030                1035

Ser Asn Ile Met Asn Phe Phe Lys Thr Glu Ile Thr Leu Ala Asn
            1040                1045                1050

Gly Glu Ile Arg Lys Arg Pro Leu Ile Glu Thr Asn Gly Glu Thr
            1055                1060                1065

Gly Glu Ile Val Trp Asp Lys Gly Arg Asp Phe Ala Thr Val Arg
            1070                1075                1080

Lys Val Leu Ser Met Pro Gln Val Asn Ile Val Lys Lys Thr Glu
            1085                1090                1095

Val Gln Thr Gly Gly Phe Ser Lys Glu Ser Ile Leu Pro Lys Arg
            1100                1105                1110

Asn Ser Asp Lys Leu Ile Ala Arg Lys Lys Asp Trp Asp Pro Lys
            1115                1120                1125

Lys Tyr Gly Gly Phe Asp Ser Pro Thr Val Ala Tyr Ser Val Leu
```

```
                    1130                1135                1140

Val Val Ala Lys Val Glu Lys Gly Lys Ser Lys Lys Leu Lys Ser
        1145                1150                1155

Val Lys Glu Leu Leu Gly Ile Thr Ile Met Glu Arg Ser Ser Phe
    1160                1165                1170

Glu Lys Asn Pro Ile Asp Phe Leu Glu Ala Lys Gly Tyr Lys Glu
    1175                1180                1185

Val Lys Lys Asp Leu Ile Ile Lys Leu Pro Lys Tyr Ser Leu Phe
    1190                1195                1200

Glu Leu Glu Asn Gly Arg Lys Arg Met Leu Ala Ser Ala Gly Glu
    1205                1210                1215

Leu Gln Lys Gly Asn Glu Leu Ala Leu Pro Ser Lys Tyr Val Asn
    1220                1225                1230

Phe Leu Tyr Leu Ala Ser His Tyr Glu Lys Leu Lys Gly Ser Pro
    1235                1240                1245

Glu Asp Asn Glu Gln Lys Gln Leu Phe Val Glu Gln His Lys His
    1250                1255                1260

Tyr Leu Asp Glu Ile Ile Glu Gln Ile Ser Glu Phe Ser Lys Arg
    1265                1270                1275

Val Ile Leu Ala Asp Ala Asn Leu Asp Lys Val Leu Ser Ala Tyr
    1280                1285                1290

Asn Lys His Arg Asp Lys Pro Ile Arg Glu Gln Ala Glu Asn Ile
    1295                1300                1305

Ile His Leu Phe Thr Leu Thr Asn Leu Gly Ala Pro Ala Ala Phe
    1310                1315                1320

Lys Tyr Phe Asp Thr Thr Ile Asp Arg Lys Arg Tyr Thr Ser Thr
    1325                1330                1335

Lys Glu Val Leu Asp Ala Thr Leu Ile His Gln Ser Ile Thr Gly
    1340                1345                1350

Leu Tyr Glu Thr Arg Ile Asp Leu Ser Gln Leu Gly Gly Asp
    1355                1360                1365

<210> SEQ ID NO 60
<211> LENGTH: 9
<212> TYPE: PRT
<213> ORGANISM: Artificial Sequence
<220> FEATURE:
<223> OTHER INFORMATION: HA tag

<400> SEQUENCE: 60

Tyr Pro Tyr Asp Val Pro Asp Tyr Ala
1               5

<210> SEQ ID NO 61
<211> LENGTH: 7
<212> TYPE: PRT
<213> ORGANISM: Artificial Sequence
<220> FEATURE:
<223> OTHER INFORMATION: nuclear localization signal

<400> SEQUENCE: 61

Pro Lys Lys Lys Arg Lys Val
1               5

<210> SEQ ID NO 62
<211> LENGTH: 1396
<212> TYPE: PRT
<213> ORGANISM: Artificial Sequence
<220> FEATURE:
```

<223> OTHER INFORMATION: HA-NLS-dCas9-NLS

<400> SEQUENCE: 62

```
Met Tyr Pro Tyr Asp Val Pro Asp Tyr Ala Ser Pro Lys Lys Lys Arg
1               5                   10                  15

Lys Val Glu Ala Ser Asp Lys Lys Tyr Ser Ile Gly Leu Ala Ile Gly
            20                  25                  30

Thr Asn Ser Val Gly Trp Ala Val Ile Thr Asp Glu Tyr Lys Val Pro
        35                  40                  45

Ser Lys Lys Phe Lys Val Leu Gly Asn Thr Arg His Ser Ile Lys
    50                  55                  60

Lys Asn Leu Ile Gly Ala Leu Leu Phe Asp Ser Gly Glu Thr Ala Glu
65                  70                  75                  80

Ala Thr Arg Leu Lys Arg Thr Ala Arg Arg Tyr Thr Arg Arg Lys
                85                  90                  95

Asn Arg Ile Cys Tyr Leu Gln Glu Ile Phe Ser Asn Glu Met Ala Lys
                100                 105                 110

Val Asp Asp Ser Phe Phe His Arg Leu Glu Glu Ser Phe Leu Val Glu
            115                 120                 125

Glu Asp Lys Lys His Glu Arg His Pro Ile Phe Gly Asn Ile Val Asp
    130                 135                 140

Glu Val Ala Tyr His Glu Lys Tyr Pro Thr Ile Tyr His Leu Arg Lys
145                 150                 155                 160

Lys Leu Val Asp Ser Thr Asp Lys Ala Asp Leu Arg Leu Ile Tyr Leu
                165                 170                 175

Ala Leu Ala His Met Ile Lys Phe Arg Gly His Phe Leu Ile Glu Gly
                180                 185                 190

Asp Leu Asn Pro Asp Asn Ser Asp Val Asp Lys Leu Phe Ile Gln Leu
            195                 200                 205

Val Gln Thr Tyr Asn Gln Leu Phe Glu Glu Asn Pro Ile Asn Ala Ser
    210                 215                 220

Gly Val Asp Ala Lys Ala Ile Leu Ser Ala Arg Leu Ser Lys Ser Arg
225                 230                 235                 240

Arg Leu Glu Asn Leu Ile Ala Gln Leu Pro Gly Glu Lys Lys Asn Gly
                245                 250                 255

Leu Phe Gly Asn Leu Ile Ala Leu Ser Leu Gly Leu Thr Pro Asn Phe
                260                 265                 270

Lys Ser Asn Phe Asp Leu Ala Glu Asp Ala Lys Leu Gln Leu Ser Lys
            275                 280                 285

Asp Thr Tyr Asp Asp Asp Leu Asp Asn Leu Leu Ala Gln Ile Gly Asp
    290                 295                 300

Gln Tyr Ala Asp Leu Phe Leu Ala Ala Lys Asn Leu Ser Asp Ala Ile
305                 310                 315                 320

Leu Leu Ser Asp Ile Leu Arg Val Asn Thr Glu Ile Thr Lys Ala Pro
                325                 330                 335

Leu Ser Ala Ser Met Ile Lys Arg Tyr Asp Glu His His Gln Asp Leu
                340                 345                 350

Thr Leu Leu Lys Ala Leu Val Arg Gln Gln Leu Pro Glu Lys Tyr Lys
            355                 360                 365

Glu Ile Phe Phe Asp Gln Ser Lys Asn Gly Tyr Ala Gly Tyr Ile Asp
    370                 375                 380

Gly Gly Ala Ser Gln Glu Glu Phe Tyr Lys Phe Ile Lys Pro Ile Leu
385                 390                 395                 400
```

-continued

Glu Lys Met Asp Gly Thr Glu Glu Leu Leu Val Lys Leu Asn Arg Glu
             405                 410                 415

Asp Leu Leu Arg Lys Gln Arg Thr Phe Asp Asn Gly Ser Ile Pro His
         420                 425                 430

Gln Ile His Leu Gly Glu Leu His Ala Ile Leu Arg Arg Gln Glu Asp
         435                 440                 445

Phe Tyr Pro Phe Leu Lys Asp Asn Arg Glu Lys Ile Glu Lys Ile Leu
     450                 455                 460

Thr Phe Arg Ile Pro Tyr Tyr Val Gly Pro Leu Ala Arg Gly Asn Ser
465                 470                 475                 480

Arg Phe Ala Trp Met Thr Arg Lys Ser Glu Glu Thr Ile Thr Pro Trp
                 485                 490                 495

Asn Phe Glu Glu Val Val Asp Lys Gly Ala Ser Ala Gln Ser Phe Ile
             500                 505                 510

Glu Arg Met Thr Asn Phe Asp Lys Asn Leu Pro Asn Glu Lys Val Leu
         515                 520                 525

Pro Lys His Ser Leu Leu Tyr Glu Tyr Phe Thr Val Tyr Asn Glu Leu
     530                 535                 540

Thr Lys Val Lys Tyr Val Thr Glu Gly Met Arg Lys Pro Ala Phe Leu
545                 550                 555                 560

Ser Gly Glu Gln Lys Lys Ala Ile Val Asp Leu Leu Phe Lys Thr Asn
                 565                 570                 575

Arg Lys Val Thr Val Lys Gln Leu Lys Glu Asp Tyr Phe Lys Lys Ile
             580                 585                 590

Glu Cys Phe Asp Ser Val Glu Ile Ser Gly Val Glu Asp Arg Phe Asn
         595                 600                 605

Ala Ser Leu Gly Thr Tyr His Asp Leu Leu Lys Ile Ile Lys Asp Lys
     610                 615                 620

Asp Phe Leu Asp Asn Glu Glu Asn Glu Asp Ile Leu Glu Asp Ile Val
625                 630                 635                 640

Leu Thr Leu Thr Leu Phe Glu Asp Arg Glu Met Ile Glu Glu Arg Leu
                 645                 650                 655

Lys Thr Tyr Ala His Leu Phe Asp Asp Lys Val Met Lys Gln Leu Lys
             660                 665                 670

Arg Arg Arg Tyr Thr Gly Trp Gly Arg Leu Ser Arg Lys Leu Ile Asn
         675                 680                 685

Gly Ile Arg Asp Lys Gln Ser Gly Lys Thr Ile Leu Asp Phe Leu Lys
     690                 695                 700

Ser Asp Gly Phe Ala Asn Arg Asn Phe Met Gln Leu Ile His Asp Asp
705                 710                 715                 720

Ser Leu Thr Phe Lys Glu Asp Ile Gln Lys Ala Gln Val Ser Gly Gln
                 725                 730                 735

Gly Asp Ser Leu His Glu His Ile Ala Asn Leu Ala Gly Ser Pro Ala
             740                 745                 750

Ile Lys Lys Gly Ile Leu Gln Thr Val Lys Val Val Asp Glu Leu Val
         755                 760                 765

Lys Val Met Gly Arg His Lys Pro Glu Asn Ile Val Ile Glu Met Ala
     770                 775                 780

Arg Glu Asn Gln Thr Thr Gln Lys Gly Gln Lys Asn Ser Arg Glu Arg
785                 790                 795                 800

Met Lys Arg Ile Glu Glu Gly Ile Lys Glu Leu Gly Ser Gln Ile Leu
                 805                 810                 815

Lys Glu His Pro Val Glu Asn Thr Gln Leu Gln Asn Glu Lys Leu Tyr

-continued

```
              820                 825                830
Leu Tyr Tyr Leu Gln Asn Gly Arg Asp Met Tyr Val Asp Gln Glu Leu
              835                 840                845
Asp Ile Asn Arg Leu Ser Asp Tyr Asp Val Asp Ala Ile Val Pro Gln
850                 855                860
Ser Phe Leu Lys Asp Asp Ser Ile Asp Asn Lys Val Leu Thr Arg Ser
865                 870                875                880
Asp Lys Asn Arg Gly Lys Ser Asp Asn Val Pro Ser Glu Glu Val Val
                  885                890                895
Lys Lys Met Lys Asn Tyr Trp Arg Gln Leu Leu Asn Ala Lys Leu Ile
              900                 905                910
Thr Gln Arg Lys Phe Asp Asn Leu Thr Lys Ala Glu Arg Gly Gly Leu
              915                 920                925
Ser Glu Leu Asp Lys Ala Gly Phe Ile Lys Arg Gln Leu Val Glu Thr
              930                 935                940
Arg Gln Ile Thr Lys His Val Ala Gln Ile Leu Asp Ser Arg Met Asn
945                 950                955                960
Thr Lys Tyr Asp Glu Asn Asp Lys Leu Ile Arg Glu Val Lys Val Ile
                  965                970                975
Thr Leu Lys Ser Lys Leu Val Ser Asp Phe Arg Lys Asp Phe Gln Phe
                  980                985                990
Tyr Lys Val Arg Glu Ile Asn Asn  Tyr His His Ala His  Asp Ala Tyr
                  995                 1000                1005
Leu Asn Ala Val Val Gly Thr  Ala Leu Ile Lys Lys  Tyr Pro Lys
1010                1015                1020
Leu Glu  Ser Glu Phe Val Tyr  Gly Asp Tyr Lys Val  Tyr Asp Val
1025                1030                1035
Arg Lys  Met Ile Ala Lys Ser  Glu Gln Glu Ile Gly  Lys Ala Thr
1040                1045                1050
Ala Lys  Tyr Phe Phe Tyr Ser  Asn Ile Met Asn Phe  Phe Lys Thr
1055                1060                1065
Glu Ile  Thr Leu Ala Asn Gly  Glu Ile Arg Lys Arg  Pro Leu Ile
1070                1075                1080
Glu Thr  Asn Gly Glu Thr Gly  Glu Ile Val Trp Asp  Lys Gly Arg
1085                1090                1095
Asp Phe  Ala Thr Val Arg Lys  Val Leu Ser Met Pro  Gln Val Asn
1100                1105                1110
Ile Val  Lys Lys Thr Glu Val  Gln Thr Gly Gly Phe  Ser Lys Glu
1115                1120                1125
Ser Ile  Leu Pro Lys Arg Asn  Ser Asp Lys Leu Ile  Ala Arg Lys
1130                1135                1140
Lys Asp  Trp Asp Pro Lys Lys  Tyr Gly Gly Phe Asp  Ser Pro Thr
1145                1150                1155
Val Ala  Tyr Ser Val Leu Val  Val Ala Lys Val Glu  Lys Gly Lys
1160                1165                1170
Ser Lys  Lys Leu Lys Ser Val  Lys Glu Leu Leu Gly  Ile Thr Ile
1175                1180                1185
Met Glu  Arg Ser Ser Phe Glu  Lys Asn Pro Ile Asp  Phe Leu Glu
1190                1195                1200
Ala Lys  Gly Tyr Lys Glu Val  Lys Lys Asp Leu Ile  Ile Lys Leu
1205                1210                1215
Pro Lys  Tyr Ser Leu Phe Glu  Leu Glu Asn Gly Arg  Lys Arg Met
1220                1225                1230
```

-continued

```
Leu Ala Ser Ala Gly Glu Leu Gln Lys Gly Asn Glu Leu Ala Leu
        1235                1240                1245

Pro Ser Lys Tyr Val Asn Phe Leu Tyr Leu Ala Ser His Tyr Glu
    1250                1255                1260

Lys Leu Lys Gly Ser Pro Glu Asp Asn Glu Gln Lys Gln Leu Phe
    1265                1270                1275

Val Glu Gln His Lys His Tyr Leu Asp Glu Ile Ile Glu Gln Ile
    1280                1285                1290

Ser Glu Phe Ser Lys Arg Val Ile Leu Ala Asp Ala Asn Leu Asp
    1295                1300                1305

Lys Val Leu Ser Ala Tyr Asn Lys His Arg Asp Lys Pro Ile Arg
    1310                1315                1320

Glu Gln Ala Glu Asn Ile Ile His Leu Phe Thr Leu Thr Asn Leu
    1325                1330                1335

Gly Ala Pro Ala Ala Phe Lys Tyr Phe Asp Thr Thr Ile Asp Arg
    1340                1345                1350

Lys Arg Tyr Thr Ser Thr Lys Glu Val Leu Asp Ala Thr Leu Ile
    1355                1360                1365

His Gln Ser Ile Thr Gly Leu Tyr Glu Thr Arg Ile Asp Leu Ser
    1370                1375                1380

Gln Leu Gly Gly Asp Ser Pro Lys Lys Lys Arg Lys Val
    1385                1390                1395

<210> SEQ ID NO 63
<211> LENGTH: 62
<212> TYPE: PRT
<213> ORGANISM: Homo sapiens

<400> SEQUENCE: 63

Arg Thr Leu Val Thr Phe Lys Asp Val Phe Val Asp Phe Thr Arg Glu
1               5                   10                  15

Glu Trp Lys Leu Leu Asp Thr Ala Gln Gln Ile Val Tyr Arg Asn Val
            20                  25                  30

Met Leu Glu Asn Tyr Lys Asn Leu Val Ser Leu Gly Tyr Gln Leu Thr
        35                  40                  45

Lys Pro Asp Val Ile Leu Arg Leu Glu Lys Gly Glu Glu Pro
    50                  55                  60

<210> SEQ ID NO 64
<211> LENGTH: 1468
<212> TYPE: PRT
<213> ORGANISM: Artificial Sequence
<220> FEATURE:
<223> OTHER INFORMATION: HA-NLS-dCas9-NLS-KRAB

<400> SEQUENCE: 64

Met Tyr Pro Tyr Asp Val Pro Asp Tyr Ala Ser Pro Lys Lys Lys Arg
1               5                   10                  15

Lys Val Glu Ala Ser Asp Lys Lys Tyr Ser Ile Gly Leu Ala Ile Gly
            20                  25                  30

Thr Asn Ser Val Gly Trp Ala Val Ile Thr Asp Glu Tyr Lys Val Pro
        35                  40                  45

Ser Lys Lys Phe Lys Val Leu Gly Asn Thr Asp Arg His Ser Ile Lys
    50                  55                  60

Lys Asn Leu Ile Gly Ala Leu Leu Phe Asp Ser Gly Glu Thr Ala Glu
65                  70                  75                  80
```

```
Ala Thr Arg Leu Lys Arg Thr Ala Arg Arg Arg Tyr Thr Arg Arg Lys
                85                  90                  95

Asn Arg Ile Cys Tyr Leu Gln Glu Ile Phe Ser Asn Glu Met Ala Lys
            100                 105                 110

Val Asp Asp Ser Phe Phe His Arg Leu Glu Glu Ser Phe Leu Val Glu
            115                 120                 125

Glu Asp Lys Lys His Glu Arg His Pro Ile Phe Gly Asn Ile Val Asp
130                 135                 140

Glu Val Ala Tyr His Glu Lys Tyr Pro Thr Ile Tyr His Leu Arg Lys
145                 150                 155                 160

Lys Leu Val Asp Ser Thr Asp Lys Ala Asp Leu Arg Leu Ile Tyr Leu
                165                 170                 175

Ala Leu Ala His Met Ile Lys Phe Arg Gly His Phe Leu Ile Glu Gly
            180                 185                 190

Asp Leu Asn Pro Asp Asn Ser Asp Val Asp Lys Leu Phe Ile Gln Leu
            195                 200                 205

Val Gln Thr Tyr Asn Gln Leu Phe Glu Glu Asn Pro Ile Asn Ala Ser
210                 215                 220

Gly Val Asp Ala Lys Ala Ile Leu Ser Ala Arg Leu Ser Lys Ser Arg
225                 230                 235                 240

Arg Leu Glu Asn Leu Ile Ala Gln Leu Pro Gly Glu Lys Lys Asn Gly
                245                 250                 255

Leu Phe Gly Asn Leu Ile Ala Leu Ser Leu Gly Leu Thr Pro Asn Phe
                260                 265                 270

Lys Ser Asn Phe Asp Leu Ala Glu Asp Ala Lys Leu Gln Leu Ser Lys
            275                 280                 285

Asp Thr Tyr Asp Asp Asp Leu Asp Asn Leu Leu Ala Gln Ile Gly Asp
290                 295                 300

Gln Tyr Ala Asp Leu Phe Leu Ala Ala Lys Asn Leu Ser Asp Ala Ile
305                 310                 315                 320

Leu Leu Ser Asp Ile Leu Arg Val Asn Thr Glu Ile Thr Lys Ala Pro
                325                 330                 335

Leu Ser Ala Ser Met Ile Lys Arg Tyr Asp Glu His His Gln Asp Leu
            340                 345                 350

Thr Leu Leu Lys Ala Leu Val Arg Gln Gln Leu Pro Glu Lys Tyr Lys
            355                 360                 365

Glu Ile Phe Phe Asp Gln Ser Lys Asn Gly Tyr Ala Gly Tyr Ile Asp
            370                 375                 380

Gly Gly Ala Ser Gln Glu Glu Phe Tyr Lys Phe Ile Lys Pro Ile Leu
385                 390                 395                 400

Glu Lys Met Asp Gly Thr Glu Glu Leu Leu Val Lys Leu Asn Arg Glu
                405                 410                 415

Asp Leu Leu Arg Lys Gln Arg Thr Phe Asp Asn Gly Ser Ile Pro His
            420                 425                 430

Gln Ile His Leu Gly Glu Leu His Ala Ile Leu Arg Arg Gln Glu Asp
            435                 440                 445

Phe Tyr Pro Phe Leu Lys Asp Asn Arg Glu Lys Ile Glu Lys Ile Leu
            450                 455                 460

Thr Phe Arg Ile Pro Tyr Tyr Val Gly Pro Leu Ala Arg Gly Asn Ser
465                 470                 475                 480

Arg Phe Ala Trp Met Thr Arg Lys Ser Glu Glu Thr Ile Thr Pro Trp
                485                 490                 495

Asn Phe Glu Glu Val Val Asp Lys Gly Ala Ser Ala Gln Ser Phe Ile
```

```
                500             505             510
Glu Arg Met Thr Asn Phe Asp Lys Asn Leu Pro Asn Glu Lys Val Leu
            515                 520                 525

Pro Lys His Ser Leu Leu Tyr Glu Tyr Phe Thr Val Tyr Asn Glu Leu
        530                 535                 540

Thr Lys Val Lys Tyr Val Thr Glu Gly Met Arg Lys Pro Ala Phe Leu
545                 550                 555                 560

Ser Gly Glu Gln Lys Lys Ala Ile Val Asp Leu Leu Phe Lys Thr Asn
                565                 570                 575

Arg Lys Val Thr Val Lys Gln Leu Lys Glu Asp Tyr Phe Lys Lys Ile
            580                 585                 590

Glu Cys Phe Asp Ser Val Glu Ile Ser Gly Val Glu Asp Arg Phe Asn
        595                 600                 605

Ala Ser Leu Gly Thr Tyr His Asp Leu Leu Lys Ile Ile Lys Asp Lys
610                 615                 620

Asp Phe Leu Asp Asn Glu Glu Asn Glu Asp Ile Leu Glu Asp Ile Val
625                 630                 635                 640

Leu Thr Leu Thr Leu Phe Glu Asp Arg Glu Met Ile Glu Glu Arg Leu
                645                 650                 655

Lys Thr Tyr Ala His Leu Phe Asp Asp Lys Val Met Lys Gln Leu Lys
            660                 665                 670

Arg Arg Arg Tyr Thr Gly Trp Gly Arg Leu Ser Arg Lys Leu Ile Asn
        675                 680                 685

Gly Ile Arg Asp Lys Gln Ser Gly Lys Thr Ile Leu Asp Phe Leu Lys
690                 695                 700

Ser Asp Gly Phe Ala Asn Arg Asn Phe Met Gln Leu Ile His Asp Asp
705                 710                 715                 720

Ser Leu Thr Phe Lys Glu Asp Ile Gln Lys Ala Gln Val Ser Gly Gln
                725                 730                 735

Gly Asp Ser Leu His Glu His Ile Ala Asn Leu Ala Gly Ser Pro Ala
            740                 745                 750

Ile Lys Lys Gly Ile Leu Gln Thr Val Lys Val Val Asp Glu Leu Val
        755                 760                 765

Lys Val Met Gly Arg His Lys Pro Glu Asn Ile Val Ile Glu Met Ala
770                 775                 780

Arg Glu Asn Gln Thr Thr Gln Lys Gly Gln Lys Asn Ser Arg Glu Arg
785                 790                 795                 800

Met Lys Arg Ile Glu Glu Gly Ile Lys Glu Leu Gly Ser Gln Ile Leu
                805                 810                 815

Lys Glu His Pro Val Glu Asn Thr Gln Leu Gln Asn Glu Lys Leu Tyr
            820                 825                 830

Leu Tyr Tyr Leu Gln Asn Gly Arg Asp Met Tyr Val Asp Gln Glu Leu
        835                 840                 845

Asp Ile Asn Arg Leu Ser Asp Tyr Asp Val Asp Ala Ile Val Pro Gln
850                 855                 860

Ser Phe Leu Lys Asp Asp Ser Ile Asp Asn Lys Val Leu Thr Arg Ser
865                 870                 875                 880

Asp Lys Asn Arg Gly Lys Ser Asp Asn Val Pro Ser Glu Glu Val Val
                885                 890                 895

Lys Lys Met Lys Asn Tyr Trp Arg Gln Leu Leu Asn Ala Lys Leu Ile
            900                 905                 910

Thr Gln Arg Lys Phe Asp Asn Leu Thr Lys Ala Glu Arg Gly Gly Leu
        915                 920                 925
```

```
Ser Glu Leu Asp Lys Ala Gly Phe Ile Lys Arg Gln Leu Val Glu Thr
            930                 935                 940

Arg Gln Ile Thr Lys His Val Ala Gln Ile Leu Asp Ser Arg Met Asn
945                 950                 955                 960

Thr Lys Tyr Asp Glu Asn Asp Lys Leu Ile Arg Glu Val Lys Val Ile
                965                 970                 975

Thr Leu Lys Ser Lys Leu Val Ser Asp Phe Arg Lys Asp Phe Gln Phe
            980                 985                 990

Tyr Lys Val Arg Glu Ile Asn Asn Tyr His His Ala His Asp Ala Tyr
            995                 1000                1005

Leu Asn Ala Val Val Gly Thr Ala Leu Ile Lys Lys Tyr Pro Lys
    1010                1015                1020

Leu Glu Ser Glu Phe Val Tyr Gly Asp Tyr Lys Val Tyr Asp Val
    1025                1030                1035

Arg Lys Met Ile Ala Lys Ser Glu Gln Glu Ile Gly Lys Ala Thr
    1040                1045                1050

Ala Lys Tyr Phe Phe Tyr Ser Asn Ile Met Asn Phe Phe Lys Thr
    1055                1060                1065

Glu Ile Thr Leu Ala Asn Gly Glu Ile Arg Lys Arg Pro Leu Ile
    1070                1075                1080

Glu Thr Asn Gly Glu Thr Gly Glu Ile Val Trp Asp Lys Gly Arg
    1085                1090                1095

Asp Phe Ala Thr Val Arg Lys Val Leu Ser Met Pro Gln Val Asn
    1100                1105                1110

Ile Val Lys Lys Thr Glu Val Gln Thr Gly Gly Phe Ser Lys Glu
    1115                1120                1125

Ser Ile Leu Pro Lys Arg Asn Ser Asp Lys Leu Ile Ala Arg Lys
    1130                1135                1140

Lys Asp Trp Asp Pro Lys Lys Tyr Gly Gly Phe Asp Ser Pro Thr
    1145                1150                1155

Val Ala Tyr Ser Val Leu Val Val Ala Lys Val Glu Lys Gly Lys
    1160                1165                1170

Ser Lys Lys Leu Lys Ser Val Lys Glu Leu Leu Gly Ile Thr Ile
    1175                1180                1185

Met Glu Arg Ser Ser Phe Glu Lys Asn Pro Ile Asp Phe Leu Glu
    1190                1195                1200

Ala Lys Gly Tyr Lys Glu Val Lys Lys Asp Leu Ile Ile Lys Leu
    1205                1210                1215

Pro Lys Tyr Ser Leu Phe Glu Leu Glu Asn Gly Arg Lys Arg Met
    1220                1225                1230

Leu Ala Ser Ala Gly Glu Leu Gln Lys Gly Asn Glu Leu Ala Leu
    1235                1240                1245

Pro Ser Lys Tyr Val Asn Phe Leu Tyr Leu Ala Ser His Tyr Glu
    1250                1255                1260

Lys Leu Lys Gly Ser Pro Glu Asp Asn Glu Gln Lys Gln Leu Phe
    1265                1270                1275

Val Glu Gln His Lys His Tyr Leu Asp Glu Ile Ile Glu Gln Ile
    1280                1285                1290

Ser Glu Phe Ser Lys Arg Val Ile Leu Ala Asp Ala Asn Leu Asp
    1295                1300                1305

Lys Val Leu Ser Ala Tyr Asn Lys His Arg Asp Lys Pro Ile Arg
    1310                1315                1320
```

```
Glu Gln Ala Glu Asn Ile Ile His Leu Phe Thr Leu Thr Asn Leu
    1325                1330                1335

Gly Ala Pro Ala Ala Phe Lys Tyr Phe Asp Thr Thr Ile Asp Arg
    1340                1345                1350

Lys Arg Tyr Thr Ser Thr Lys Glu Val Leu Asp Ala Thr Leu Ile
    1355                1360                1365

His Gln Ser Ile Thr Gly Leu Tyr Glu Thr Arg Ile Asp Leu Ser
    1370                1375                1380

Gln Leu Gly Gly Asp Ser Pro Lys Lys Lys Arg Lys Val Met Asp
    1385                1390                1395

Ala Lys Ser Leu Thr Ala Trp Ser Arg Thr Leu Val Thr Phe Lys
    1400                1405                1410

Asp Val Phe Val Asp Phe Thr Arg Glu Glu Trp Lys Leu Leu Asp
    1415                1420                1425

Thr Ala Gln Gln Ile Val Tyr Arg Asn Val Met Leu Glu Asn Tyr
    1430                1435                1440

Lys Asn Leu Val Ser Leu Gly Tyr Gln Leu Thr Lys Pro Asp Val
    1445                1450                1455

Ile Leu Arg Leu Glu Lys Gly Glu Glu Pro
    1460                1465

<210> SEQ ID NO 65
<211> LENGTH: 545
<212> TYPE: DNA
<213> ORGANISM: Homo sapiens

<400> SEQUENCE: 65
cgggagtaac ctccaccgca ccccaccgct ccgaggggca gccggcccgg cccgagtttc        60
tccccagaag cctccagccg cggctctcgg ggaggaggaa ggaaggggtt ccccgtccag       120
gaagcagcac cagcggcgac cgcctccagc ctcaccctcc tcagcccgc accgcccatt       180 cctcactccc cgcgccgccg cgtccgcgcg cctcccccct gcagacccct ctcacccagc       240
ccgccccgac cccgcgcccg cgccccccac ccgcccctcc ggggacccct aattcattca       300
ctcgccgccg ccccgcccg gcgccggcaa agagggtcgg gacccgggca ggggcccagg       360
aggggtggtc cgctccgtac ctctctcccg cacctgggag ccgctgagcc tctggccccg       420
ccgccgcctt cagtgcctgc gccgcgctcg ctcccagtcc gaaatggcgg gggccgggag       480
tactggccga gccgccgcca ccttcgccgc cgccactgcc gccgccgctg ctgcctccgc       540
cgccg                                                                   545
```